US005733760A

United States Patent [19]
Lu et al.

[11] Patent Number: 5,733,760
[45] Date of Patent: Mar. 31, 1998

[54] SALMONELLA VECTORS ENCODING TRUNCATED PAG FUSION PROTEIN, METHOD OF MAKING, AND USES THEREOF

[75] Inventors: Yichen Lu, Cambridge; Samuel I. Miller, Brookline; Kevin Killeen, Milton, all of Mass.

[73] Assignees: Virus Research Institute, Cambridge; The General Hospital Corporation, Boston, both of Mass.

[21] Appl. No.: 286,767

[22] Filed: Aug. 5, 1994

[51] Int. Cl.⁶ .......................... C12N 15/00; C12N 15/63; A61K 39/21; A61K 39/112
[52] U.S. Cl. .................. 435/172.3; 435/245; 435/252.3; 435/320.1; 424/185.1; 424/190.1; 424/192.1; 424/200.1; 424/208.1; 424/234.1; 424/258.1
[58] Field of Search ................................ 435/172.3, 245, 435/252.3, 320.1; 424/185.1, 190.1, 192.1, 200.1, 208.1, 234.1, 258.1

[56] References Cited

PUBLICATIONS

Miller, S.I. et al. 1993 . . . "The PhoP virulence regulon and live oral Salmonella vaccines." Vaccine 11(2):122–125.
Allan, J.S., et al., Science 228:1091–1093 (1985).
Arendrup, M., et al., JAIDS 5:303–307 (1992).
Arya, S., et al., Science 229:69–73 (1985).
Barre-Sinoussi, F., et al., Science 220:868–871 (1983).
Berkower, I., et al., J. Exp. Med. 170:1681–1695 (1989).
Berman, P., et al., Nature 345:622–625 (1990).
Buchmeier, N.A., et al., Infect. Immun. 57:1–7 (1989).
Carter, et al., J. Exp. Med. 139:1189 (1974).
Clavel, F., et al. AIDS 1:135–140 (1987).
Cohen, E.A., et al. Nature 344:532–534 (1988).
Cohen, E.A., et al., JAIDS 3:11–18 (1990).
Dalgleish, A.G., et al., Nature 312:763–767 (1984).
Daniel, M.D., et al., Science 228:1201–1204 (1985).
Dayton, A., et al., Cell 44:941–947 (1986).
Desrosiers, R.C., et al., Ann. Rev. Immunol. 8:557–558 (1990).
Emerman, M., et al., Cell 57:1155–1165 (1989).
Emini, E., et al., Nature 355:728–730 (1992).
Fisher, A.G., et al., Nature 320:367–371 (1986).
Fisher, A.G., et al., Science 237:888–893 (1987).
Gallo, R.C., et al., Science 224: 500–503 (1984).
Gegerfelt, A., et al., Virology 185:162–168 (1991).
Hattori, N., et a., Proc. Natl. Acad. Sci. USA, 87:8080–8084 (1990).
Helseth, E., et al., J. Virol. 64:2416–2420 (1990).
Henderson, L.E., et al., Science 241:199–201 (1988).
Ho, D., et al., J. Virol. 65:489–493 (1991).
Hook, et al., Harrison's Principals of Internal Medicine, 9th Ed., 641–848, McGraw Hill, NY (1980).
Hornick, R.B., et al., N. Eng. J. Med. 283:686–691, 739–746 (1970).
Hu, W., et al., Virology 173:624–630 (1989).
Javaherian, K., et al., Science 250:1590–1593 (1990).
Kang, C–Y., et al., Proc. Natl. Acad. Sci. U.S.A. 88:6171–6175 (1991).
Kappes, J.C., et al., Virology 184:197–209(1991).
Kestler, H.W., et al., Cell 65:651–662 (1991).
Klatzmann, D., et al., Nature 312:767–768 (1984).
Klimkait, T., et al., J. Virol. 64:621–629 (1990).
Kowalski, K., et al., J. Virol. 65:281–291 (1991).
Leonard, C., et al., J. Biol. Chem. 265:10373–10382 (1990).
Letvin, N.L., et al., Science 230:71–73 (1985).
Lifson, J.D., et al., Nature 323:725–728 (1986).
Linsley, P., et al., J. Virol. 62:3695–3702 (1988).
Malim, M., et al., Nature 338:254–257 (1989).
Matthews, T., et al., Proc. Natl. Acad. Sci. U.S.A. 83:9709–9713 (1986).
Nara, P., et al., J. Virol. 64:3779–3791 (1990).
Ohno, T., et al., Proc. Natl. Acad. Sci. U.S.A. 88:10726–10729 (1991).
Profy, A., et al., J. Immunol. 144:4641–4647 (1990).
Robey, W.G., et al., Science 228:593–595 (1985).
Sarin, et al., Vaccine Research, 3(1):49–57 (1994).
Skinner, M., et al., J. Virol. 62:4195–4200 (1988).
Sodroski, J., et al., Nature 322:470–474 (1986).
Sodroski, J., et al., Nature 321:412–417 (1986).
Sodroski, J., et al., Science 229:74–77 (1985).
Sodroski, J., et al., Science 231:1549–1553 (1986).
Steimer, K.S., et al., Science 254:105–108 (1991).
Strebel, K., et al., J. Virol. 63:3784–3791 (1989).
Strebel, K., et al., Nature 328:728–730 (1987).
Strebel, K., et al., Science 241:1221–1223 (1988).
Terwilliger, E.F., et al. Proc. Natl. Acad. Sci. U.S.A. 86:5163–5167 (1989).
Thali, M., et al., J. Virol. 65:6188–6193 (1991).
WHO meeting, Vaccine 8:425–437 (1991).
Weis, R.A., et al., Nature 324:572–575 (1986).
Willey, R., et al., J. Virol. 66:226–234 (1992).
Yu, X–F, et al., J. Virol. 64:5688–5693 (1990).

*Primary Examiner*—James C. Housel
*Assistant Examiner*—Rodney P. Swartz
*Attorney, Agent, or Firm*—Ronald I. Eisenstein; David S. Resnick

[57] ABSTRACT

A modified Salmonella, wherein the wild type pag gene such as pagC has been replaced by a gene encoding a truncated pag gene such as pagC gene fused to a heterologous DNA segment, is disclosed. This modification significantly attenuates the virulence of the Salmonella. In addition, immune reaction to the portion of the fusion protein encoded by the heterologous gene can be generated. Uses of the vector, including its use in a drug screen are also disclosed.

13 Claims, 11 Drawing Sheets

```
         10         20         30         40         50         60         70
GTTAACCACT CTTAATAATA ATGGGTTTTA TAGCGAAATA GACTTTTTTA TCGCGTGTTC TATTGCG 80         90        100        110        120        130        140
TTAGTTATTA TTTTTTTGGA ATGTAAATTC TCTCTAAACA CAGGTGATAT TTATGTTGGA TTGTGGTGT 150        160        170        180        190        200        210
TGATTCTATT CTTATAATAT AACAAGAAAT GTTGTAACTG ATAGATATAT TAAAAGATTA AATCGGAGCG
                       * ────────▶

220        230        240        250        260        270        280
GGAATAAAGC GTGCTAAGCA TCATCGTGAA TATGATTACA GCGCCTGCGA TGGCATATAA CCGTATTGCG 290        300        310        320        330        340        350
GATGGAGCGT CACGTGAGGA CTGTGAAGCA CAATGCGATA TGTTCTGATT ATATGGCGAG TTTGCTTAAT 360        370        380        390        400        410        420
GACATGTTTT TAGCCGAACG GTGTCAAGTT TCTTAATGTG GTTGTGAGAT TTTCTCTTTA AATATCAAAA 430        440        450        460        470        480        490
TGTTGCATGG GTGATTTGTT GTTCTATAGT GGCTAAACAC TTTATGGTTT CTGTTAAATA TATATGCGTG 500        510        520        530        540        550        560
AGAAAAATTA GCATTCAAAT CTATAAAAGT TAGATGACAT TGTAGAACCG GTTACCTAAA TGAGCGATAG 570        580        590        600        610        620        630
AGTGCTTCGG TAGTAAAAAT ATCTTTCAGG AAGTAAACAC ATCAGGAGCG ATAGCGGTGA ATTATTCGTG 640        650        660        670        680        690        700
GTTTTGTCGA TTCGGCATAG TGGCGATAAC TGAATGCCGG ATCGGTACTG CAGGTGTTTA AACACACCGT 710        720        728
AAATAATAAG TAGTATTAAG GAGTTGTT
```

```
ATG AAA AAT ATT ATT TTA TCC ACT TTA GTT ATT ACT ACA AGC GTT TTG GTT GTA      782
MET LYS ASN ILE ILE LEU SER THR LEU VAL ILE THR THR SER VAL LEU VAL VAL       18
                                              ▼
AAT GTT GCA CAG GCC GAT ACT AAC GCC TTT TCC GTG GGG TAT GCA CGG TAT GCA      836
ASN VAL ALA GLY ALA ASP THR ASN ALA PHE SER VAL GLY TYR ALA ARG TYR ALA       36
                      ▲
CAA AGT AAA GTT CAG GAT TTC AAA AAT ATC CGA GGG GTA AAT GTG AAA TAC CGT      890
GLN SER LYS VAL GLN ASP PHE LYS ASN ILE ARG GLY VAL ASN VAL LYS TYR ARG       54

TAT GAG GAT GAC TCT CCG GTA AGT TTT ATT TCC TCG CTA AGT TAC TTA TAT GGA      944
TYR GLU ASP ASP SER PRO VAL SER PHE ILE SER SER LEU SER TYR LEU TYR GLY       72

GAC AGA CAG GCT TCC GGG TCT GTT GAG CCT GAA GGT ATT CAT TAC CAT GAC AAG      998
ASP ARG GLN ALA SER GLY SER VAL GLU PRO GLU GLY ILE HIS TYR HIS ASP LYS       90

TTT GAG GTG AAG TAC GGT TCT TTA ATG GTT GGG CCA GCC TAT CGA TTG TCT GAC     1052
PHE GLU VAL LYS TYR GLY SER LEU MET VAL GLY PRO ALA TYR ARG LEU SER ASP      108

AAT TTT TCG TTA TAC GCG CTG GCG GGT GTC GGC ACG GTA AAG GCG ACA TTT AAA     1106
ASN PHE SER LEU TYR ALA LEU ALA GLY VAL GLY THR VAL LYS ALA THR PHE LYS      126

GAA CAT TCC ACT CAG GAT GGC GAT TCT TTT TCT AAC AAA ATT TCC TCA AGG AAA     1160
GLU HIS SER THR GLN ASP GLY ASP SER PHE SER ASN LYS ILE SER SER ARG LYS      144

ACG GGA TTT GCC TGG GGC GCG GGT GTA CAG ATG AAT CCG CTG GAG AAT ATC GTC     1214
THR GLY PHE ALA TRP GLY ALA GLY VAL GLN MET ASN PRO LEU GLU ASN ILE VAL      162
```

FIG. 5-1

```
GTC GAT GTT GGG TAT GAA GGA AGC AAC ATC TCC TCT ACA AAA ATA AAC GGC TTC  1268
VAL ASP VAL GLY TYR GLU GLY SER ASN ILE SER SER THR LYS ILE ASN GLY PHE   180

AAC GTC GGG GTT GGA TAC CGT TTC TGA AAAGC                                 1300
ASN VAL GLY VAL GLY TYR ARG PHE                                            188

1310       1320       1330       1340       1350       1360       1370
ATAAGCTATG CGGAAGGTTC GGGTTCCGCA CCCCCAGTCA ATAAAACAGG GCTTCTTTAC CAGTGACACC 1380       1390       1400       1410       1420       1430       1440
TACCTGCGTG TCTTTTCTCT CTTCCTCATA CTCTCTTCGT CATAGTGACG CTGTACATAA CATCTCACTA 1450       1460       1470       1480       1490       1500       1510
GCATAAGCAC AGATAAAGCA TTGTGGTAAG CAATCAAGGT TGCTCAGGTA GGTGATAAGC AGGAAGGAAA 1520       1530       1540       1550       1560       1570       1580
ATCTGGTGTA ATAACGCCA GATCTCACAA GATTCACTCT GAAAAATTTT CCTGGAATTA ATCACAATGT 1590       1600       1610       1620       1630       1640       1650
CATCAAGATT TTGTCACCGC CTTCGCATAT TGTACCTGGGG CTGAACGAC TACTGAAAAG TAGCAAGGTA

1660       ·1670      1680       1690       1700       1710       1720
TGTATTTTAT CCAGGAGAGC ACCTTTTTTG CGCCTGGCAG AAGTCCCCAG CCGCCACTAG CTCAGCTGGA 1730       1740       1750       1760       1770       1780       1790
TAGAGCAICA ACCTCCTAA GTTGATGGTCC GAGGTTCGAG CCCTCCCTGG CCCTCCAATG TGGTTATCCT 1800       1810       1820       1830       1840       1850       1860
ATAATGTTAT TACCTCAGT GTCAGGCTGAT GATCTGGGTT CGACTCCCAC TGACCACTTC AGTTTTGAAT 1870       1880       1890       1900       1910       1920       1930
AAGTATTCTC TCCCAACCC TOTTACAGAAT AATTTCATTT ATTACGTGAC AAGATAGTCA TTTATAAAAA 1940       1950       1960       1970       1980       1990       2000
ATGCACAAAA ATGTTATTC TCTTTTATTAC TTGTGAGTTG TAGATTTTTC TTATGCGGTG AAUCCCCCTT 2010       2020       2030       2040       2050       2060       2070
TGCGGCGGGG CCTCCAGTC AAATAGTTAAT GTTCCTCGCG AACCATATTG ACTCTCCTAT GCTTCACCGG 2080       2090       2100       2110       2120       2130       2140
GAGGCACCCG GCACCGCAA TTTTTTATAAA ATGAAATTCA CACCCTATGG TTCAGAGCGG TCTCTTTTTA 2150       2160       2170       2180       2190       2200       2210
CATCAGGTGG GCAAGCATA ATGCAGGTTAA CTTGAAAGAT ACCATCAATA GCAGAAACCA GTGATTTCCT 2220       2230       2240       2250       2260       2270       2280
TTATGGCCTG GGGATTTAA CCGCGCCAGAG CGTATGCAAG ACCCTGGCGC GGTTGGCCGG TGATCCTTCA 2290       2300       2310
ATAGTGCGAA TATGAAIGG TTACCAGCCGC TGCGAATTC
```

FIG. 5-2

SALMONELLA VECTORS ENCODING TRUNCATED PAG FUSION PROTEIN, METHOD OF MAKING, AND USES THEREOF

The present invention relates to Salmonella vectors encoding a fusion protein containing a truncated pagC gene (phosphatase activated gene C) fused to a heterologous gene, and uses thereof.

Salmonella species cause a spectrum of clinical disease that include enteric fevers and acute gastroenteritis [Hook, et al., Harrison's Principals of Internal Medicine, 9th Ed., 641–848, McGraw Hill, N.Y. (1980)]. Salmonella infections are typically acquired by oral ingestion. The organism traverses the stomach and replicates in the small intestine. [Hornick, et al., N. Eng. J. Med. 283:688 (1970)]. The bacteria are capable of invasion of intestinal mucosal cells. For example, S. typhi can pass through the mucosal barrier and spread via the Peyer's patches to the lamina propria and regional lymph nodes.

In this family are numerous strains having different host ranges. For example, S. typhi, which causes typhoid fever can only infect man [Hook, et al., supra]. S. enteriditis, S. typhimurium infect a wider range of hosts causing acute gastroenteritis in man and a disease similar to typhoid fever in mice and cows. Thus, this species has been used as a laboratory model of S. typhi and typhoid fever [Carter, et al., J. Exp. Med. 139:1189 (1984)].

The majority of infectious agents utilize mucosal surfaces as the primary portal of entry. Thereafter, the organism either remains localized at the mucosal surfaces or disseminates to establish a systemic infection. Following infection, the host develops both systemic and mucosal protective immune responses against the infectious agent. Therefore, a preferred vaccine for the prevention of mucosally transmitted agents like HIV-1 should effect primary protection at the mucosal site of entry and secondary protection from systemic spread.

Salmonella has been proposed as one means of providing effective delivery of desired antigens. They provide the advantage that they can be delivered orally. The bacteria grow rapidly and do not require growth in cell culture. Thus, large scale production of vectors, for example, in the use of vaccines, can be accomplished more quickly and easy then where mammalian tissue cultures are required. Furthermore, Salmonella are facultative intracellular parasites with the ability to invade and survive within host processing cells [Buchmeier, N. A., et al., Infect. Immun. 57:1–7 (1989)]. After peroral ingestion, Salmonella are concentrated within the liver, spleen, bone marrow, and the Peyers' patches of the gut-associated lymphoid tissue (GALT), which are organs rich in reticuloendothelial antigen processing cells [Hornick, R. B., et al., N. Eng. J. Med. 283:686–691, 739–746 (1970)].

Genetic attenuation of live infectious organisms has been demonstrated as a highly effective method for developing efficacious vaccines against a single pathogen. Examples of successfully attenuated vaccines include vaccinia, delivered by scarification, poliomyelitis and GCG, delivered orally, and Measles, mumps and rubella, delivered parenterally.

Recent efforts at deriving live vaccine vectors have concentrated on the development of viral vectors such as attenuated vaccinia virus and bacterial vectors such as BCG and Salmonella species [WHO meeting, Vaccine 8:425–437 (1991)]. A central concern in the development of live viral vectors is the problem of reactogenicity in an immunocompromised human host. The lack of viricidal agents makes it difficult to arrest generalized infections. By contrast, bacterial vectors are more easily controlled because a wide variety of antibiotics are available should a live bacterial vaccine exhibit unanticipated virulence in an immunocompromised individual.

Human immunodeficiency virus type 1 (HIV-1) and, to a lesser extent, human immunodeficiency virus type 2 (HIV-2) are etiologic agents of acquired immune deficiency syndrome (AIDS) in humans [Barre-Sinoussi, F., et al., Science 220:868–871 (1983) Gallo, R. C., et al., Science 224:500–503 (1984); Clavel, F., et al. AIDS 1:135–140 (1987)]. These viruses are related to simian immunodeficiency viruses that infect feral populations of sooty mangabeys, African green monkeys, and mandrills [Desrosiers, R. C., et al., Ann. Rev. Immunol. 8:557–558 (1990)]. A simian immunodeficiency virus ($SIV_{mac}$) capable of infecting and inducing an AIDS-like disease in macaques is closely related to HIV-2 and $SIV_{smm}$ [Letvin, N. L. et al., Science 230:71–73 (1985); Daniel, M. D., et al., Science 228:1201–1204 (1985)].

The primate immunodeficiency viruses establish persistent infections in their hosts even in the face of an antiviral immune response. Part of this ability may reside in the capacity of these viruses to tightly regulate expression of the viral proteins, as evidenced by the presence of four conserved regulatory genes in all members of this group of retroviruses.

In addition to the gag, pro, pol and env genes typical of retroviruses, these viruses contain vif, tat, rev, and nef genes [Haseltine, W., et al., Raven Press (1990)]. The tat protein stimulates the viral LTR to express viral RNA [Arya, S., et al., Science 229:69–73 (1985); Sodroski, J., et al., Science 229:74–77 (1985)] while the rev protein promotes the nuclear egress of viral messenger RNA's encoding the structural gene products [Emerman, M., et al., Cell 57:1155–1165 (1989); Malim, M., et al., Nature 338:254–257 (1989)]. Both tat and rev genes are essential for viral replication [Dayton, A., et al., Cell 44:941–947 (1986); Fisher, A. G., et al., Nature 320:367–371 (1986); Sodroski, J., et al., Nature 321:412–417 (1986)]. The vif and nef genes, although dispensable for virus replication in some tissues culture settings, are well conserved [Sodroski, J., et al., Science 231:1549–1553 (1986); Fisher, A. G., et al., Science 237:888–893 (1987); Strebel, K., et al., Nature 328:728–730 (1987); Kestler, H. W., et al., Cell 65:651–662 (1991)]. Depending upon the particular primate immunodeficiency virus, vpx, vpr, and/or vpu genes are also present in the proviral DNA [Desrosier, R. C., et al., Ann. Rev. Immunol. 8:557–578 (1990); Haseltine W., et al., Raven Press (1990)]. These genes are also dispensable for virus replication in tissue culture. The vpx and vpr proteins are incorporated into virions and are believed to play a positive role in the early phase of the virus life cycle [Cohen, E. A., et al., JAIDS 3:11–18 (1990); Yu, X-F, et al., J. Virol. 64:5688–5693 (1990); Henderson, L. E., et al., Science 24 1:199–201 (1988); Hu, W., et al., Virology 173:624–630 (1989); Kappes, J. C., et al., Virology 184:197–209 (1991); Hattori, N., eta., Proc. Natl. Acad. Sci. USA, 87:8080–8084 (1990)]. The vpu gene is found only in HIV-1 and encodes a 15–20 kD protein, depending upon the virus isolate [Terwilliger, E. F., et al., Proc. Natl. Acad. Sci, U.S.A. 86:5163–5167 (1989); Cohen, E. A., et al. Nature 344:532–534 (1988); Strebel, K., et al., Science 241:1221–1223 (1988); Klimkait, T., et al., J. Virol. 64:621–629 (1990)]. The vpu protein is associated with the host cell membranes and facilitates the redistribution of viral proteins from inside the infected cell to free virion particles

[Terwilliger, E. F., et al., *Proc. Natl. Acad. Sci. U.S.A.* 86:5163–5167 (1989); Cohen, E. A., et al., *Nature* 344:532–534 (1988); Strebel, K., et al., *Science* 241:1221–1223 (1988); Klimkait, T., et al., *J. Virol.* 64:621–629 (1990); Strebel, K., et al., *J. Virol.* 63:3784–3791 91989)]. Thus, the major function of the vpu product is to modulate virus release, although other effects of vpu on envelope glycoprotein or CD4 steady state levels have been observed [Willey, R., et al., *J. Virol.* 66:226–234 (1992); Kimura T., and Karn J. personal communication]. The in vivo function of the vpu protein is unknown.

The persistence of primate immunodeficiency virus infection is also made possible by the particular features of the viral envelope glycoproteins. The viral glycoproteins are synthesized as a 160 Kd precursor, which is cleaved intracellularly to yield the gp 120 exterior envelope glycoprotein and the gp 41 transmembrane glycoprotein [Allan, J. S., et al., *Science* 228:1091–1093 (1985)]. Robey, W. G., et al., *Science* 228:593–595 (1985)]. The gp120 glycoprotein binds the CD receptor, following which the gp120 and gp41 glycoproteins in concert contribute to the membrane fusion process [Klatzmann, D., et al., *Nature* 312:767–768 (1984); Dalgleish, A. G., et al., *Nature* 312:763–767 (1984); Helseth, E., et al., *J. Virol.* 64:2416–2420 (1990)]. The latter process mediates both virus entry and viral cytopathic effect, which consists of multinucleated giant cell (syncytium) formation and single cell lysis [Sodroski, J., et al., *Nature* 322:470–474 (1986); Lifson, J. D., et al., *Nature* 323:725–728 (1986); Kowalski, K., et al., *J. Virol.* 65:281–291 (1991)]. The exterior envelope glycoproteins of these viruses are heavily glycosylated and contain regions of hyper-variability, most of which are thought to consist of disulfide-linked loops exposed to the exterior of the protein [Leonard, C., et al., *J. Biol. Chem.* 265:10373–10382 (1990)]. In the case of HIV-1, most of the neutralizing antibody response elicited early in the course of infection is directed against the third variable (V3) loop of the gp120 glycoprotein [Nara, P., et al., *Proc. Ouatreime Colloque des Cent Gardes* (Girard, Valette, eds. Paris: Pasteur Vaccins) pp. 203–215 (1989)]. These antibodies inhibit some aspect of the membrane fusion process [Skinner, M., et al., *J. Virol.* 62:4195–4200 (1988); Linsley, P., et al., *J. Virol* 62:3695–3702 (1988)]. Neutralization is generally strain-restricted due to variation on the V3 region, but some antibodies recognize better conserved elements near the tip of the loop [Ohno, T., et al., *Proc. Natl. Acad. Sci. U.S.A.* 88:10726–10729 (1991); Matthews, T., et al., *Proc. Natl. Acad. Sci. U.S.A.* 83:9709–9713 (1986); Javaherian, K., et al., *Science* 250:1590–1593 (1990)]. The anti-V3 loop antibodies are protective against intravenous challenge by homologous HIV-1 [Berman, P., et al., *Nature* 345:622–625 (1990); Emini, E., et al., *Nature* 355:728–730 (1992)]. Later in the course of HIV-1 infection, antibodies that neutralize a broader range of HIV-1 isolates are generated [Weis, R. A., et al., *Nature* 324:572–575 (1986); Profy, A., et al., *J. Immunol.* 144:4641–4647 (1990); Berkower, L, et al., *J. Exp. Med.* 170:1681–1695 (1989)]. These antibodies recognize discontinuous epitopes near the CD4 binding site of gp120 and block the binding of gp120 to CD4 [Ho, D., et al., *J. Virol.* 65:489–493 (1991); Kang, C-Y., et al., *Proc. Natl. Acad. Sci. U.S.A.* 88:6171–6175 (1991); Steimer, K. S., et al., *Science* 254:105–108 (1991)]. The epitopes for some of these antibodies have been mapped by extensive mutagenesis, and depend upon amino acids located in all five conserved gp120 regions [Thali, M., et al., *J. Virol.* 65:6188–6193 (1991)]. These neutralizing antibodies do not keep virus replication in check indefinitely, probably because of virus variation and selection of neutralization-resistant viruses and because of immunosuppression and compromised ability of the host to respond to novel epitopes [Nara, P., et al., *J. Virol.* 64:3779–3791 (1990); Gegerfelt, A., et al., *Virology* 185:162–168 (1991); Arendrup, M., et al., *JAIDS* 5:303–307 (1992)].

A variety of models for treating diseases, including AIDS, have been proposed. It was reported that at the Second International Conference on Vaccines:New Technologies and Applications, held in Alexandria, Va., a variety of proposals were presented. It was reported that Dr. Jonah Salk of the Salk Institute for Biological Studies in San Diego, Calif., claimed that Th1 (T-helper cell type 1) memory maintenance is the key for controlling HIV infection. Thus, in achieving a useful vaccine, it was explained that the goal should be to stimulate and maintain cell-mediated immunity (CMI) not humoral immunity. Dr. Salk further claimed that because of cross-regulation a T-helper cell type 2 (Th2) antibody response actually inhibits the generation of cell-mediated immunity. Thus, the loss of CMI memory occurring from the body mounting a Th2 response was alleged to actually help the virus. [GENETIC ENGINEERING NEWS, vol. 14: 1, 24 (1994)].

Accordingly, it would be useful to develop methods for preferentially stimulating a Th1 response as opposed to a Th2 response for specific antigens. It would also be useful to have a drug screen to assay for compounds that enhance and/or potentiate the Th1 response. It would also be useful to have a vector that could be used to selectively express an antigen in a particular organ such as a macrophage.

SUMMARY OF THE INVENTION

We have now discovered a vector that can be used to selectively express a particular antigen in a desired organ, such as a macrophage.

We have discovered that a Salmonella vector containing a sufficient portion of a Salmonella genome for replication and infection, wherein a native wild type pag gene, preferably pagC, in the Salmonella genome has been modified to contain a deletion in the pag gene, and wherein said modified pag gene is linked in frame to a heterologous DNA segment to create a gene encoding a pag-fusion protein (e.g. a pagC-fusion protein gene), wherein the pag-fusion protein gene is operably linked to an in vivo inducible promoter significantly attenuates the virulence of Salmonella. Preferably, the fusion protein encodes a viral antigen such as a lentivirus antigen (e.g. an HIV antigen). A preferred fusion protein encodes a pagC-HIV envelope fusion protein.

This modification of the pag gene, e.g. pagC gene, can be used to attenuate a Salmonella bacteria which can then be used in a number of ways including as a vaccine.

One can also use the vector in an assay for a compound that enhances an antigen specific T-helper cell type (Th1) response comprising:

(a) innoculating an animal with the vector;

(b) administering a test compound;

(c) comparing the results with a first control animal administered the vector but not the test compound, and a second control animal administered the test compound but not administered the vector; and (d) determining the difference in Th1 response.

BRIEF DESCRIPTION OF THE DRAWINGS

FIG. 5 is a map of the DNA sequence of the pagC region (SEQ ID NO:1) and the deduced amino acid sequence (SEQ ID NO:3).

In FIG. 6, lane 1 is the HI407 cells infected with SL102 that contains the pagC-HIV fusion protein. Lane 2 is the HI407 cell without infection. Lane 3 is the cells infected with SL102 in which the pagC and HIV envelope genes are not fused. A detectable band in lane 1 represents the pagC-HIV fusion protein as detected by anti-gp120 antibody.

DETAILED DESCRIPTION OF THE INVENTION

Figure 1:
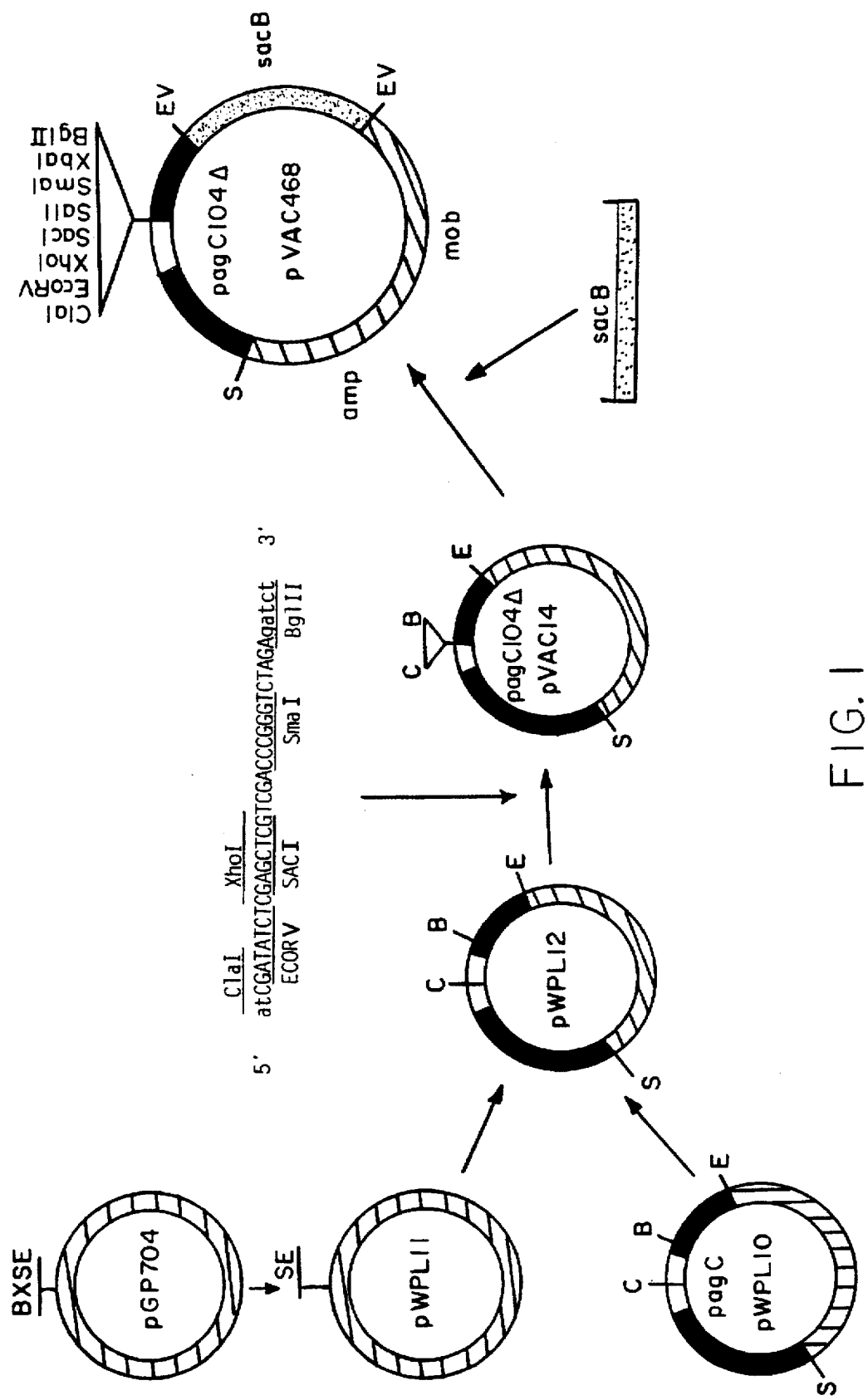
FIG. 1 is a schematic showing the construction of the vector pVAC468. Symbols (B) BgI II, (C) ClaI, (E) EcoRI, (S) SphI, (V) EcoRV, and (X) XbaI. Plasmid regions; (black) Salmonella DNA, (white) pagC gene, (horizontal stripes) pGP704 vector, (vertical stripes) pWPL10 vector, (stippled) sacB gene.

Salmonella vectors have been proposed for use as live attenuated vaccines. They offer the advantage of providing a bacterial vector, which can be controlled by use of antibiotics, should any unanticipated virulence occur in a patient. The Salmonella vaccine currently available, Ty21a, however, suffers from the deficiencies of requiring four doses to acquire immunity, the nature of the attenuation is chemical and not known, another proposed vaccine suffers from being invasive and having some incidence of systemic spread. Accordingly, improved Salmonella vectors have been proposed. One vector, which does not result in transient bacteremia does so as a result of a first mutation in the phoP regulon. The regulon is composed of two genes present in the operon, phoP and phoQ. The phoP and phoQ gene products are highly similar to other members of bacterial two-component transcriptional regulators that respond to environmental stimuli. They control the expression of a large number of other genes. In addition to the two regulatory genes, there are a large number of structural genes, whose expression is regulated by phoP and phoQ. For example, a phoP regulatory region repressed gene (prg) or a phoP regulated activated genes (pag). By mutations in these regions, preferably by a deletion, the Salmonella is rendered less virulent. Preferably, a second mutation in an aromatic amino acid synthetic gene, such as aroA, or aroC/aroD locus is made.

One proposed site in the phoP regulon is to make a deletion of the pagC gene. Surprisingly, while partial deletions of this gene and ligation to another gene thereby creating a fusion protein attenuates this region, a deletion of the entire gene does not effect virulence. We have also discovered that other pag genes, e.g. pagD, behave in a similar manner.

Accordingly, the present invention is directed to a vector comprising a deletion of a portion of a pag gene, for example, the pagC gene, which is then linked in the appropriate frame with another DNA segment encoding a desired heterologous gene to express a fusion protein. In order to create the fusion protein, the deletion is preferably from the portion encoding the carboxy terminus of the gene. One can create a deletion in any of the pag genes, such as the pagC gene of up to the entire structural gene as long as the signal sequences are encoded in the resultant fusion protein. In pagC this is at about nucleotide 827 (i.e. amino acid 34). Preferably, one deletes at least about 300–700 nucleotides from the gene. More preferably, at least about 450–600 nucleotides. Still more preferably, at least about 450–550 nucleotides. Alternative strategies for mutating the pag gene include internal deletions of the portions of the gene, for example, encoding the pagC transmembrane domains. The deletion in the pagC gene must be sufficient to attenuate the vector by an order of magnitude of at least $10^2$, more preferably by at least $10^3$. This can readily be determined by a murine screen using an *S. typhimurium strain*. For example, one can inject mice with identical vectors except for the deletion and determine $LD_{50}$ by standard means. With one embodiment where there is a deletion of 490 nucleotides, as shown in FIG. 3 and as described in detail infra, the $LD_{50}$ goes from 2 to 20,000 as a result of the deletion.

The skilled artisan can readily link a heterologous gene in frame to the truncated pagC sequence by standard means. The vector preferably contains a convenient insertion site at the deletion to be able to insert any desired DNA segment encoding any heterologous protein. For example, one can insert a linker, e.g. a polylinker, with convenient restriction sites.

In the present invention any Salmonella strain can be used, for example, *S. typhi, S. enteriditis, S. typhimurium*, and *S. choleraesuis*. The Salmonella cell may be of any serotype, including *S. typhimurium, S. paratyphi A, S. paratyphi B, S. paratypi C, S. pylorum, S. dublin, S. heidelberg, S. newport, S. minnesota, S. infantis, S. virchow* and *S. panama*. Preferably, the vector is a *S. typhi* vector or *S. enteriditis typhimurium*. More preferably, the vector is a *S. typhi* vector.

Construction of attenuated *Salmonella typhi* and *typhimurium* expressing the HIV-1 antigen as an in vivo inducible gene such as a macrophage inducible gene can readily be accomplished based upon the present disclosure.

A preferred method of insertion of the foreign gene into Salmonella vector utilizes homologous recombination between the DNA sequences present both in the chromosome and on a shuttle plasmid. Consequently, a double recombinant event results in a site specific insertion of the foreign sequences and a coincidental deletion of a specific bacterial locus. The shuttle plasmid is preferably designed to be unable to replicate within Salmonella without being integrated into the chromosome. This can be done by a number of means including those described below. The recombinant bacteria can be selected by use of a two step procedure. Firstly, the bacteria that acquire the shuttle plasmid sequences through a single recombination event, merodiploid, can be selected utilizing a selectable marker encoded by the shuttle plasmid. This selectable marker should preferably be positioned in the plasmid such that its subsequent loss can identify the bacteria in which a second recombination event has condensed the final double recombinant structure by excising a portion containing the marker.

A group of genes in Salmonella are activated in macrophage. Among them, pagC (phosphatase activated gene C) is transcriptionally activated about 100 fold [Alpuche-Aranda, C., et al. *Proc. Natl. Acad. Sci, U.S.A.* 89:10079–10083 (1992)]. For example, a derivative of pJM703.1 described in Miller et al., *J. Bact.* 170:2572 (1988), hereby incorporated by reference can be used to prepare the vector. This vector is an R6K derivative with a deletion in the pir gene. As a result of this deletion, R6K derivatives require the pir gene product to replicate. This can be supplied by vectors such as an *E. coli* containing the pir gene as a lambda bacteriophage prophage to support replication. Cells that do not contain a pir gene will not support replication of the vector as a plasmid. This vector also contains the mob region of RP4 which will allow mobilization into other gram negative bacteria by mating from *E. coli* strains such as SM 10lambda p/r, which can provide the mobilization function in trans. A salmonella shuttle plasmid can be used to create the deletion in the desired Salmonella strain. For example, pVAC468, whose construction is described in Miller, S. I., et al., *Vaccine* 11:122–125 (1993) (which is incorporated herein by reference] and whose construction is exemplified in FIG. 1) can be used. As shown in FIGS. 1–3, pVAC468 contains a fragment of salmonella genomic DNA including the pagC promoter and its 5' flanking sequences (about 1400 bp), a truncated pagC gene, which lacks the last 80 amino acid, and 800 bp of the 3' flanking sequences. In addition, the plasmid has the ampicillin resistant gene and the sacB gene, the expression of which in the presence of sucrose is toxic to the bacteria, as selectable markers. A polylinker containing multiple restriction endonuclease sties is inserted at the end of the truncated pagC gene.

FIG. 2 shows a general method for creating a Salmonella truncated pagC fusion-protein. FIG. 3 shows how to prepare a fusion protein with HIV envelope-protein.

In the vector, virtually any heterologous gene can be used to form pagC-fusion protein. When one wants to generate an immune reaction to the heterologous gene one can insert "genes" encoding protein fragments as long as they contain a desired epitope. Additionally, one can also insert multiple genes, e.g., gag-pol. One can express an antigen to generate an immune reaction. For example, the antigen can be to a bacteria, a virus or a parasite. Preferably, the heterologous DNA segment encodes a protein or antigenic fragment thereof that is at least about 60 amino acids, more preferably, the heterologous genes preferably include a gene encoding immunogenic lentiviral antigen such as a portion of HIV envelope protein, HIV gag protein, HIV nef protein, a viral antigen for persistent infections such as hepatitis B surface antigen, hepatitis C surface antigen, etc. A preferred DNA segment encodes conserved epitopic regions such as an HIV-1 envelope protein encoding the conserved epitopic regions of the envelope protein. For example, such a gene segment preferably encodes a part of the HIV envelope glycoprotein containing the principle neutralizing domain (PND). A group of synthetic peptide derived from the PND have been reported to elicit neutralizing antibody in animals [Javaherian, K., et al. *Proc. Natl. Acad. Sci. U.S.A.*, 86:6768–6772 (1989)]. The glycosylation of the PND, which is absent in an HIV-1 envelope protein expressed in bacteria, such as Salmonella, should not be required for establishing protective immunity. Such a DNA fragment can readily be prepared from any HIV strain. For example, a DNA fragment derived from $HIV_{LAI}$ envelope gene, $HIV_{BRU}$, $HIV_{IIIB}$, etc. including the PND, but not the signal sequences and the first 220 amino acids can be cloned into a convenient restriction site in a plasmid for use in the invention.

These vectors will produce large amounts of the heterologous gene.

In addition, one can design vectors containing heterologous gene in multiple sites and also expressing multiple truncated pag-fusion proteins.

For example, the DNA fragment containing an HIV-HXB2 envelope gene, except for its signal and its first 220 amino acid can be prepared by a range of techniques including being generated by PCR and inserted into a restriction site such as the SmaI site to make a in frame fusion between the pagC gene and the HIV-1 gene. The new Salmonella shuttle plasmid, named pVACHIVE3, can be confirmed by DNA sequencing. As a control to show that expression of HIV gene is directed by the pagC promoter, plasmid pVACHIVE3fs can be constructed in which an additional base is added between pagC and HIV genes so that HIV gene is frame shifted from the pagC gene, thereby establishing the importance of creating a fusion protein to attenuate the bacteria by this deletion.

The pagC region is shown in FIGS. 4 and 5. FIG. 4 shows the restriction endonuclease sites of the pagC locus. The heavy bar indicates pagC coding sequence. The TnphoA insertion is indicated by an inverted triangle. The direction of transcription is indicated by the arrow and is left to right. The numbers indicate the location of endonuclease sites, in number of base pairs, relative to the start codon of predicted pagC translation with positive numbers indicating location downstream of the start codon and negative numbers indicating location upstream of the start codon. A is AccI, B is BglI, C is ClaI, D is DraI, E is EcoRI, H is HpaI, N is NruI, P is PstI, S is SspI, T is StuI, U is PvuII, V is EcoRv, and II is BglII. FIG. 5 shows the DNA sequence (SEQ ID NO:1) and translation of pagC::TnphoA (SEQ ID NO.3). The heavy underlined sequence indicates a potential ribosomal binding site. The single and double underlines indicate sequences in which primers were constructed complementary to these nucleotides for primer extension of RNA analysis. The asterisk indicates the approximate start of transcription. The arrow indicates the direction of transcription. The boxed sequences indicate a region that may function in polymerase binding and recognition. The inverted triangle is the site of the sequenced TnphoA insertion junction. The arrow indicates a potential site for single sequence cleavage.

Vectors containing the appropriate deletions in the pagC region can readily be made. For example, 3 kilobases of DNA containing the pagC gene (i.e. from the PstI restriction endonuclease site 1500 nucleotides 5' to the start of pagC translation to the EcoRI restriction endonuclease site 1585 nucleotides downstream of pagC translation termination) can be inserted into the pJM703.1 derivative discussed above. One can then use appropriate restriction enzymes to cleave nucleotides encoding the carboxy-portion of the pagC protein. Thereafter, one can use standard techniques to create a unique site so a heterologous gene can readily be inserted in-frame with the remaining portion of the gene to produce a pagC-fusion protein. For example, the pagC sequence from the ClaI restriction endonuclease site can be deleted (this is a 490 nucleotide segment) and replaced with a synthetic oligonucleotide polylinker that creates unique restriction endonuclease sites. DNA encoding one or more heterologous proteins, or fragments thereof, e.g., an antigen, such as HIV envelope, can be inserted into this site. The resultant vector can be used for the insertion of multiple foreign genes into the DNA surrounding pagC in any Salmonella species because this gene is highly conserved.

The pir vector can then be mobilized into Salmonella by mating or any other delivery technique, e.g., heat shock, bacteriophage transduction or electroporation. Since the vector does not replicate, it can only be inserted into Salmonella by site specific recombination with the homologous DNA on both sides of the pagC gene. This disrupts and inactivates the native pagC locus by replacing it with the disrupted pagC DNA carried on the vector.

Recombination events can be identified by standard techniques such as using marker exchange and selective media as discussed above. For example, using foreign DNA inserted into the pagC locus that confers a growth advantage in a particular media. The stable introduction of antibiotic resistance genes into the resultant vector for selection is less desirable because this can allow an increase in antibiotic resistance in the natural population of bacteria. Genes which confer resistance to substances other than antibiotics, e.g., to heavy metals or arsenic (for mercury resistance, see Nucifora, et al., *J. Bact.* 171:4241–4247 (1989), hereby incorporated by reference) are preferably used for selection in place of antibiotic resistance. Alternatively, selection can be performed using a Salmonella recipient strain that carries an auxotrophic mutation in a metabolic pathway and a vector that carries a DNA sequence that complements the auxotrophic mutation. Many Salmonella live vaccine prototypes contain mutations in histidine or purine pathways. Thus, complementation of these metabolic auxotrophies can be used for selection. However, purine mutations have been shown to be too attenuated for use as a vaccine in humans. Antibiotics resistant genes can preferably be used as markers when used as part of a "suicide vector" where the loss of the gene is used for selection. Proof of marker exchange can be documented by means such as loss of the ampicillin resistance (carried on the plasmid backbone) or by blot hybridization analysis.

For example, a gene useful for selection when using a vaccine strain with a metabolic auxotrophy is described below. Specific examples include the cloning of the DNA encoding both purB and phoP by complementation of a strain deleted for function of both these genes. Salmonella gene libraries have been constructed in a pLAFR cosmid vector [Frindberg, et al., *Anal Biochem.* 137:266–267 (1984), hereby incorporated by reference], by methods known to those skilled in the art. pLAFR cosmids are broad host range plasmids which can be mobilized into Salmonella from *E. coli*. An entire bank of such strains can be mobilized into Salmonella vaccine strains and selected for complementation of an auxotrophic defect (e.g., in the case of purB growth on media without adenine). The DNA segment able to complement this defect is then identified and can be cloned into the delivery vector for the heterologous gene.

The desired heterologous genes are inserted into the vector by known techniques. For example, using a polylinker that is inserted into the truncated pagC sequence of the vector.

The heterologous genes can be under the control of any of a range of promoters (i.e. operably linked to). These promoters can readily be picked by the skilled artisan based upon the context in which the vector is used. Preferably, one would use an in vivo inducible promoter. The skilled artisan can readily select such promoters. For example, numerous environmentally regulated promoter systems can be expressed in specific environments in the host and shut off in other environments. Because the expression of foreign proteins, such as membrane proteins can be toxic to the bacterium, the use of environmentally regulated promoters that can be selectively expressed in mammalian tissues is desirable. For example, in producing large amounts of vector one would want the vector grown in the laboratory without expression of the heterologous antigen. Additionally, there are situations where one would not want the vector expressed in vivo. For example, high expression of such antigens in a host animal's tissues may result in increased attenuation of the organism by diverting the metabolic fuel of the organism to the synthesis of heterologous proteins. There are also situations where one would want the fusion protein expressed in a particular organ or cell. For example, where the foreign antigen is toxic to the host cells of the vector and its expression results in prematurely killing it before expression of the fusion protein in a desired target cell. One preferred promoter would be a macrophage-inducible promoter. We have found that various pag genes are selectively expressed in macrophages. For example, pagC-P. Thus, one could readily use their promoters. With pagC, one can use the native pagC promoter of the truncated gene for macrophage inducible expression. When one wishes to use a different promoter one can insert that promoter for the pagC promoter in the fusion protein by standard techniques based upon this disclosure. Further, being able to selectively express the vector in specified environments can be used for screens. For example, expression of the desired heterologous gene in phagocytic cells can increase the Th1 immune response to these proteins. Thus, one can use such promoters to create a model that stimulates antigen specific Th1 responses. These animals can then be used in screens for drugs that enhance and/or selectively potentiate this response.

Promoter systems that can be used include nutritionally regulated promoter systems such as those for which it has been demonstrated that a specific nutrient is not available to bacteria in mammalian hosts. For example, purines [Sigwart, et al., *Infect. Immun.* 57:1858 (1989)] and iron [Finklestein, et al., *Rev. Infect. Dis.* 5:S759 (1983)], are not available within the host. Thus, promoters that are iron regulated, such as the aerobactin gene promoter, as well as promoters for biosynthetic genes in purine pathways, may be useful. Other environmentally regulated Salmonella promoters include promoters for genes which encode proteins which are specifically expressed within macrophages, e.g., the DnaK and GroEL proteins, which are increased by growth at high temperature, as well as some phoP activated gene products [Buchmeier, et al., Science 248:730 (1990); Alpache-Aranda, C., et al., Proc. Natl. Acad. Sci. U.S.A., 89:10079–10083 (1992)] hereby incorporated by reference]. Promoters such as the pagC 5' controlling sequences and promoters for heat shock genes, e.g., GroEL and DnaK, should be activated specifically within the macrophage. The macrophage is the site of antigen processing and the expression of heat shock genes in macrophages and the wide conservation of heat shock genes in nature may explain the immunodominance of these proteins. A consensus heat shock promoter sequence is known and can be used in the vectors [Cowling, et al., Proc. Natl. Acad. Sci. USA 82:2679 (1985), hereby incorporated by reference.]

The vectors can include an environmentally regulated T7 polymerase amplification system to express heterologous proteins. For example, the T7 polymerase gene [Tabor, S., et al., Current Protocols in Molecular Biology ed. Ausubel, et al., pgs. 3.5.1.2) John Wiley, & Sons (1989), hereby incorporated by reference] under control of an iron regulated promoter, can preferably be included on the vectors described above. We have inserted the aerobactin gene promoter of E. coli with the sequence CATTTCTCAT-TGATAATGAGAATCATTATTGACATAAT-TGTTATTATTTT ACG (SEQ ID NO:2), [Delorenzo, et al., J. Bact. 169:2624, hereby incorporated by reference] in front of the T7 polymerase gene and demonstrated iron regulation of the gene product. Such vector includes one or more heterologous antigens under the control of the T7 polymerase promoters. When the organism encounters low iron T7 polymerase will be synthesized and high expression of genes with T7 promoters is facilitated.

Because the pagC gene is expressed in macrophages, the use of the pagC promoter for expression of the fusion protein is preferred where one wants to have the protein expressed in the macrophage to stimulate a Th1 response. Using these techniques one can readily prepare a vector for a specific objective. For example, a shuttle plasmid containing the desired heterologous gene can be inserted into a predetermined Salmonella strain by standard techniques such as described above. For example, the pVACHIVE3 can be introduced into a wild type Salmonella typhimurium strain, 10428, by conjugal transfer of the plasmid DNA from SM10Δpir [Simon, R., et al., Bio/Tech 1:784–791 (1983)]. As 10428 is ampicillin sensitive and the SM10Δpir can not grow efficiently on M9 medium which lacks leucine, threonine, and thiamine (M9LTT), the colonies that are able to grow on M9LTT plates with ampicillin are the 10428 hosts that have acquired the shuttle plasmid. Because the plasmid is non-replicative in the Salmonella strain, the bacteria must have acquired the plasmid DNA through a single homologous recombination between the pagC locus and the shuttle plasmid. In order to remove the wild type pagC gene and the antibiotics marker in the plasmid DNA, another homologous recombination is required, which can be selected by growing the bacteria in the presence of sucrose and the absences of sodium chloride at 30° C. At such conditions, the product of the sacB gene carried by the plasmid is toxic to the host. Therefore, the new derivatives from 10428 that are able to grow must be the bacteria that have removed the sacB gene and the wild type pagC gene through a single homologous recombination. See, FIG. 3. To confirm the selection, the bacteria are plated on both the sucrose plate and the ampicillin plate. Those colonies that are sensitive to ampicillin but able to grow on sucrose plate are selected. Southern blot and Western blot analysis can be performed to confirm the molecular construction of the new salmonella strain, e.g. named CSHIV101. By the same protocol, a second vector differing from the first by insertion of the heterologous gene out of frame such as pVACHIVE3fs can be introduced into strain 10428 to select CSHIVfs.

Because the Salmonella genome is so large one can insert other heterologous genes at other sites so that one can express multiple proteins and antigens in addition to the truncated pagC-fusion protein. For example, to potentiate a particular response one can express one or more cytokines along with the fusion protein.

To evaluate the immune response to the heterologous antigen expressed as part of the fusion protein, such as the one under the control of the pag promoters, mice can be inoculated with bacteria which expressed a pagC-HIV env fusion protein, under the control of the pagC regulatory sequences. The vector is the one described above.

Control mice can be inoculated with a vector wherein a frame shift (fs) is inserted between the pagC sequences and the HIV envelope sequences so a fusion protein is not expressed.

These strains are injected intraperitoneally into BALB/c mice. Serum samples are taken three weeks after inoculation. Normal mouse serum (MNS) can be used as a control. Standard ELISA assays are used to test the sera for the presence of HIV gp120-specific antibodies. Sera can also be tested for LPS-specific antibodies using *S. typhimurium* LPS. See FIG. 7 which shows a preclinical evaluation in mice of attenuation and immunogenicity of Salmonella-HIV strains. This vector and CSHIV101, CSHIVfs were injected in Balb/c mice by intraperitoneal injection (IP injection). The graph shows that the genetic fusion of pagC gene and HIV envelope gene significantly attenuates the pathogenic effect of *Salmonella typhimurium* in mice. However, only the fusion mutant (SCHIV101), not the deletion of pagC gene (CS468), attenuated the bacteria. With the mutant CSHIVfs, similar results to those seen for the pagC deletion mutant CS468 were shown.

The detection of anti-Salmonella and anti-gp120 is shown in FIG. 7. Different amounts of vector can be injected with the results as shown. These results indicate that the use of a vector expressing a fusion protein as disclosed herein substantially attenuates the viral vector (i.e. $LD_{50}$=20,000 for the vector expressing a fusion protein as opposed to $LD_{50}$=2 for the same vector with a frame shift so it does not produce a fusion protein. Both CSHIV101 and CSHIVfs can be tested in BALB/c mice to detect the antibody subtypes produced. FIG. 8 shows that a vector according to the present teaching produce antibodies to the heterologous protein of the fusion protein that belong to IgG2a subtype. This indicates that the fusion protein expressed by the vector stimulates a Th1 response instead of a Th2 response. See also FIG. 9 and 10.

In general, a suitable effective dose for administration of one or more vectors described herein will be in the range of $10^5$ to $10^{11}$ colony forming units. Preferably, the vector is administered as a single dose.

Administration may be by any suitable route including oral, rectal, nasal, topical (including buccal and sublingual), vaginal and parenteral (including subcutaneous, intramuscular, intravenous and intradermal) with oral being preferred. It will be appreciated that the preferred route may vary with, for example, the condition and age of the recipient.

The present invention may be used to establish a range of assays useful for screening compounds that can selectively potentiate the response to a particular antigen. These assays can be in vivo models such as with a mouse or monkey or in vitro models using transformed cell lines established by the methodology described herein and known techniques. For example, when the desired antigen is an HIV antigen such as the envelope glycoprotein a useful in vivo model can be prepared with a SHIV-infected macaque or monkey such as disclosed in U.S. patent application Ser. No. 07/887,505 which is incorporated herein by reference. Alternatively one can use mice, preferably transgenic mice such as SCID mice, and Human lymphocyte-reconstituted SCID mice.

It is also expected that the present invention can be used for prophylactic immunization of individuals, or treatment of individuals stricken with a disease carried by a particular antigen such as for treatment of HIV-1 infected individuals.

While the vectors may be administered alone, they also may be present as part of a pharmaceutical composition. The compositions of the invention comprise at least one vector together with one or more acceptable carriers, e.g., liposomes, and optionally other therapeutic ingredients. The carrier(s) must be "acceptable" in the sense of being compatible with the other ingredients of the formulation and not deleterious to the recipient thereof.

The compositions include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and in liposomes and may be prepared by any methods well known in the art of pharmacy.

Such methods include the step of bringing into association the ingredients to be administered with the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing water. Molded tablets may be made by molding in a suitable machine a mixture of the powdered compound moistened with an inert liquid diluent. The tablets may optionally be coated or scored and may be formulated so as to provide slow or controlled release of the active ingredient therein.

Compositions suitable for topical administration include lozenges comprising the ingredients in a flavored base, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Compositions suitable for topical administration to the skin may be presented as ointments, creams, gels and pastes comprising one or more combination of the compounds of formula (I) and a pharmaceutically acceptable carrier. A suitable topical delivery system is a transdermal patch containing the ingredient to be administered.

Compositions suitable for rectal administration may be presented as a suppository with a suitable base comprising, for example, cocoa butter or a salicylate.

Compositions suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tables of the kind previously described.

It should be understood that in addition to the ingredients particularly mentioned above, the formulations of this invention may include other agents conventional in the art having regard to the type of formulation in question, for example, those suitable for oral administration may include flavoring agents.

All documents mentioned herein are incorporated herein by reference.

The present invention is further illustrated by the following examples. These examples are provided to aid in the understanding of the invention and are not to be construed as limitations thereof.

Materials and Methods

Strains, media and genetic methods.

American Type Culture Collection (ATCC) strain 14028 was used as the parental strain for all the *S. typhimurium* strains described herein. The other strains used in this work are listed in Table 1.

TABLE 1

| | | |
|---|---|---|
| Plasmids | | |
| pVAC468 | pagC104Δ suicide vector | * |
| pVAC511 | pVAC468 with slt-1 B subunit gene | * |
| *E. coli* | | |
| wild type | clinical isolate | MGH bacteriology lab |
| SM10λpir | thi1, thr1, leuB6, supE44, tonA21, lacY1, recA-::RP4-2-Tc::Mu | |
| *S. typhimurium* | | |
| wild type | ATCC 14028 | ATCC |
| CS014 | pagC1::TnphoA | * |
| CS468 | pagC104Δ | * |
| SL3261 | aroA.Del407 | Bruce Stocker (ᵃ) |
| CS511 | pagC104Δ slt-1 B SL3261 | * |
| *S. typhimurium* LT2 | ATCC 15277 | ATCC |
| *S. typhimurium* Q1 | clinical isolate | J. Peterson, U. Texas |
| *S. typhi* Ty2 | Vi-positive *S. typhi* | Carolyn Hardegree/FDA |
| CS125 | pagC1:TnPhoA | * |
| Ty469/s | single recombination of pVAC468 into CS125 pagC1::TnphoA, pagC104Δ, sacB, bla | * |
| Ty469 | pagC104Δ | * |
| 522Ty | ΔaroA hisG46 in Ty2 | Bruce Stocker (ᵇ) |
| Ty476 | pagC104Δ 522Ty | * |
| 523Ty | ΔaroA hisG46 in CDC 10-80 | Bruce Stocker (ᵇ) |
| Ty475 | pagC104Δ 523Ty2 | * |
| Other Salmonellae | | |
| *Salmonella drypool* | clinical isolate | J. Peterson, U. Texas |
| *Salmonella paratyphi* A | ATCC 9150 | ATCC |
| *Salmonella paratyphi* C | ATCC 13428 | ATCC |
| *Salmonella enteriditis* | clinical isolate | Kevin Kileen |
| Other Enterobacteriaceae | | |
| *Yersinia enterocolitica* | clinical isolate | MGH bacteriology lab |
| *Vibrio cholera* | clinical isolate | Peruvian epidemic |
| *Vibrio vulnificus* | clinical isolate | MGH bacteriology lab |
| *Camphylobacter fetus* | clinical isolate | MGH bacteriology lab |
| *Citrobacter freundii* | clinical isolate | MGH bacteriology lab |
| *Klebsiella pneumoniae* | clinical isolate | MGH bacteriology lab |
| *Shigella flexneri* | clinical isolate | MGH bacteriology lab |
| *Shigella sonnei* | clinical isolate | MGH bacteriology lab |
| *Shigella dysenteriae* | clinical isolate | MGH bacteriology lab |

*Described herein
ᵃHolseth, S. K. and Stocker, B.A.D. Nature 291:238-239 (1981)
ᵇEdwards, M. F. & Stocker, B.A.D. J. Bacterioil 170:3991-1995 (1988)

Rich medium was Luria broth (LB) and minimal medium was M9 [David, R. W., et al., *Advanced Bacterial Genetics: A Manual for Genetic Engineering*, p. 203, Cold Spring Harbor Laboratory, Cold Spring Harbor, N.Y. (1980)]]. Strains with aroA and hisG mutations were grown on media supplemented with an aromatic amino acid mixture [final plate concentrations were 0.02 mM p-aminobenzoic acid, 0.02 mM dihydroxybenzoic acid, 0.02 mM p-hydroxybenzoic acid, 0.1 mM tyrosine, 0.1 mM tryptophan] and 0.1 mM histidine [Hoiseth, S. K., et al., *Nature* 291:238-239 (1981)]. *S. typhi* strains were grown on minimal media supplemented with 0.1 mM cystine as well as aromatic amino acids and antibiotics as needed. P22HTint transductions were performed as previously described [Davis, supra]. RP4 plasmid derivatives were mobilized from SM10λpir into the appropriate Salmonella strains by conjugal transfer [Simon, R., et al., *Bio/Tech.* 1:784-791 (1983)]. Sucrose selection was performed on LB plates lacking sodium chloride and supplemental with 10% sucrose [Blomfield, L, et al., *Mol. Microbiol.* 5:1447-1457 (1991)].

Molecular Biology Techniques

Chromosomal DNA was prepared by the method of Makalanos using Proteinase K instead of Pronase [Mekalanos, J. J., *Cell* 35:253-263 (1983)]. DNA, size fractionated in agarose gels, was transferred to Genescreen Plus membranes (NEN/DuPont, Boston, Mass.) for blot hybridization by the method of Southern [Southern, E. M., et al., *J. Mol. Biol.* 98:503-517 (1975)]. Radiolabeled DNA probes prepared by the random primer method [Feinberg, A. P., et al., Anal. Biochem. 132:6-13 (1983)] were hybridized to blots at 42° C. in a solution containing 1% SDS, 1M NaCl, and 50% (high stringency) or 25% (low stringency) formamide. The blots were washed in 2×SSC at room temperature, then in 2×SSC/1% SDS at 65° C., and finally in 0.1×SSC at room temperature. Plasmid DNA was transformed into *E. coli* strains by calcium chloride and heat shock [Maclachlan, P. R., et al., *J. Bacteriol.* 161:442-445 (1985)]. Plasmid preparations were done by the standard alkaline lysis method [ref. 30, p. 368-369]. DNA sequencing was performed by the dideoxy-chain termination method of Sanger, et al. [Sanger, F., et al., *Proc. Natl. Acad. Sci. USA* 74:5463-5467 (1977)] as modified for use with Sequenase (U.S. Biochemical Corp., Cleveland, Ohio). Oligonucleotides for sequencing and construction of a synthetic multiple restriction endonuclease region were synthesized on an Applied Biosystems machine. The sequences of the oligonucleotides used to construct the synthetic DNA fragments were a) 5' CGATATCTCGAGCTCGTCGAC-CCGGGTCTAGA 3' (SEQ ID NO:4) and b) 5' GATCTCTA-GACCCGGGTCGACGAGCTCGAGATCT 3' (SEQ ID:NO 5). Restriction endonucleases, T4 DNA ligase, and DNA polymerase I were purchased from New England Biolabs (Beverly, Mass.) and Bethesda Research Laboratories (Bethesda, Md.).

Protein Analysis

Periplasmic proteins were obtained from the supernatant of spheroplasts prepared as described in [Hantke, K., *Mol. Gen. Genet.* 182:288-292 (1981)]. Overnight cultures were grown in LB and LB plus 0.2 mM 2,2-dipyridyl, an iron chelator. One-dimensional protein gel electrophoresis was performed by the method of Laemmli [Laemmli, U. K., *Nature* 227:680-685 (1970)]. Proteins were transferred to a Nitrobind membrane (Micron Separations Inc.) using the Semi-phor TE70 transfer apparatus from Hoefer Scientific Instruments. Western blots and quantification of B subunit by enzyme-linked immunosorbent assay (ELISA) were done using antisera against purified Shiga toxin.

Animal Studies

Lethal doses ($LD_{50}$) were determined using female BALB/c mice obtained from Charles River Breeding Laboratories [Reed, L. J., et al. *Amer. J. Hygiene* 27:493-497 (1938)]. Overnight cultures were diluted in normal saline and injected intraperitoneally. Colony counts were confirmed by plating.

Results pagC was shown to be a unique locus in Enterobacteriaceae.

To minimize chances of recombination and transfer to environmental organisms, it is desirable to insert heterologous genes within a unique Salmonella locus. Therefore, the conservation of pagC among many Enterobacteriaceae was tested using blot hybridization. Chromosomal DNA was prepared from five Salmonella serotypes and seven other enteric species. DNA was digested with the restriction endonuclease, EcoRV, blotted to Genescreen Plus and probed with the ClaI/BglII restriction fragment of pWPL10 which is internal to pagC [Miller, V. L., et al., *Salmonellae. Infect. Immun.* 60:3763–3770 (1992)].

The pagC probe only hybridized to Salmonella DNA under high stringency conditions. pagC appeared to be present in all the Salmonella species tested, including *S. typhi* and *S. paratyphi* A and C, which are major causes of human typhoid fever. Several other strains, including *S. Typhimurium* LT2 and Q1, *S.* drypool, Vibrio vulnificus, Shigella sonnei, and Shigella dysenteriae, were tested with similar results (data not shown). In addition, chromosomal DNAs digested with a different restriction endoculease, EcoRI, were blotted and probed (data not shown). The fact that identical results were obtained with EcoR1 suggests that the lack of hybridization in non-Salmonella strains was not a result of the rare possibility of multiple EcoRV sites closely spaced within a conserved DNA region. Under conditions of low stringency, multiple cross-contaminating bands were seen in the lanes containing Salmonella DNA as well as the DNA of other enteric organisms but they were significantly less abundant. The darkest non-specific band at 18 hours was approximately 10% as dense as the pagC specific Salmonella bands after one hour (data not shown). Therefore, we concluded that by blot hybridization, pagC was unique to Salmonella species.

Construction of a Suicide Vector for the Replacement of the pagC locus.

The suicide plasmids described were RP4 replicons which require the pir protein for replication [Kolter, R., et al., *Cell* 15:1199–1208 (1978)]. When RP4 replicons, such as JM703.1 and pGP704, are mobilized into a strain which lacks pir, they cannot replicate and homologous recombination events can be recognized by selection of the plasmid encoded ampicillin resistance [Nakayama, K., et al., *Bio/Tech.* 6:693–697 (1988)]. First, pGP704 was digested with the restriction endonucleases BglII and XbaI, end-filled using the large fragment of DNA polymerase 1, and ligated using T4 ligase to form pWPL11 (See, FIG. 1). This removed restriction endonuclease sites unique to pGP704 that could be used in the construction of synthetic DNA with restriction endonuclease sites useful for cloning heterologous DNA. An approximately three kilobase SphI/EcoRI restriction endonuclease generated DNA fragment of Salmonella DNA from pWPL10 [Miller, V. L., et al., *Salmonellae. Infect. Immun.* 60:3763–3770 (1992)] containing approximately 1.5 kilobases 5' and 0.8 kilobases 3' to the pagC protein coding region was inserted into the SphI and EcoRI restriction sites of pWPL11 to construct pWPL12. DNA with multiple restriction endonuclease sites was constructed by hybridization of complementary synthetic oligonucleotides. This synthetic oligomer was ligated to pWPL12 which had been digested with the restriction endonucleases ClaI and BglII and transformed into SM10λpir.

Recombinant clones containing a plasmid with restriction endonuclease sites unique to the synthetic DNA and a 490 nucleotide deletion within the pagC locus were identified by plasmid preparation and restriction endonuclease digestion. The deletion within pagC included DNA encoding the final 84 amino acids of the pagC protein. One such clone was designated pVAC14. The insertion of the synthetic oligomer within the pagC deletion was confirmed by DNA sequencing (data not shown). pCVD442, a pGP704 derivative containing the sacB gene [Donnenberg, M. S., et al., *Infect. Immun.* 59:4310–4317 (1991)], was digested with the restriction endonucleases SalI and XbaI, end-filled using the large fragment of DNA polymerase I, and ligated to create pWPL19. The removal of these restriction endonuclease sites from pCVD442 allowed SalI and XbaI to remain unique within pVAC14. The EcoRV fragment of pWPL19, containing the sacB gene, was ligated to pVAC14 which had been digested with EcoRI and end-filled using the large fragment of DNA polymerase I. This ligation was transformed into SM10λpir and colonies were screened for sensitivity to sucrose. One such clone contained a plasmid, pVAC468, in which the acquisition of the sacB gene was documented by restriction endonuclease digestion. Therefore, we had constructed a suicide plasmid containing pagC DNA, multiple DNA endonuclease sites for cloning genes within pagC, and a selectable non-antibiotic marker for identification of loss of plasmid sequences by homologous recombination.

Use of pVAC468 to replace pagC.

pVAC468 was used to make a pagC deletion in *S. typhimurium* strain, CS014, which carries the pagC1;TnphoA allele. CSO14 was constructed using strain CS119 [Miller, S. I., et al., *Proc. Natl. Acad. Sci. USA* 86:5054–5058 (1989)] as a donor of the pagC1::TrphoA allele in a transductional cross with *S. typhimurium* strain ATCC14028 using bacteriophage P22HTint. pVA4C68 was mobilized from SM10λpir into CSO14 by conjugal transfer. Since SM10λpir is kanamycin resistant, there was no antibiotic counterselection to identify pVAC468/SM10λpir from CSO14 which had integrated pVAC468 into the chromosome. Therefore, colonies with a single homologous recombination into the pagC locus were selected on M9 medium containing ampicillin. The lack of leucine, threonine, and thiamine in the media retarded the growth of auxotrophic SM10λpir.

Figure 2:
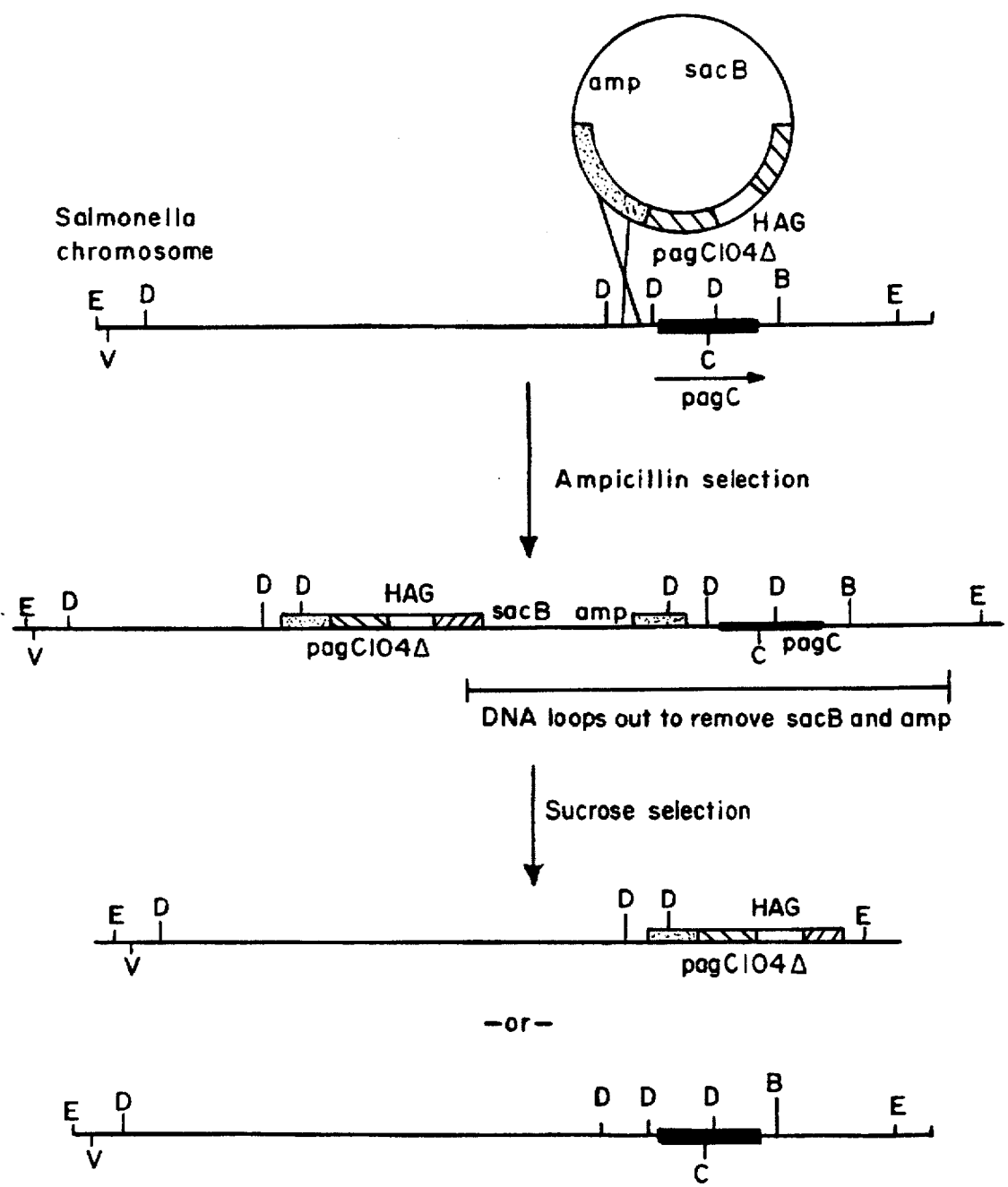
FIG. 2 is a schematic showing the use of the vector of FIG. 1 to insert a gene for a heterologous antigen into a Salmonella chromosome as part of a carboxy-truncated pagC-fusion protein. Conjugal transfer with *E. coli* mobilizes the suicide vector (pVAC468) into the Salmonella chromosome. A single homologous recombination results in a recombinant that is ampicillin resistant and sucrose sensitive. Using sucrose selection cells surviving on sucrose media will have looped out the sacB gene by homologous recombination. Sucrose resistant, ampicillin sensitive colonies are then selected for further analysis. Southern blot hybridization of chromosomal DNA from sucrose resistant strains using a pagC specific probe will show which of two possible outcomes has occurred from the second recombination event. Namely, restoration of the wild-type pagC locus or its replacement with the pagC 104 Δ insert.
Figure 3:
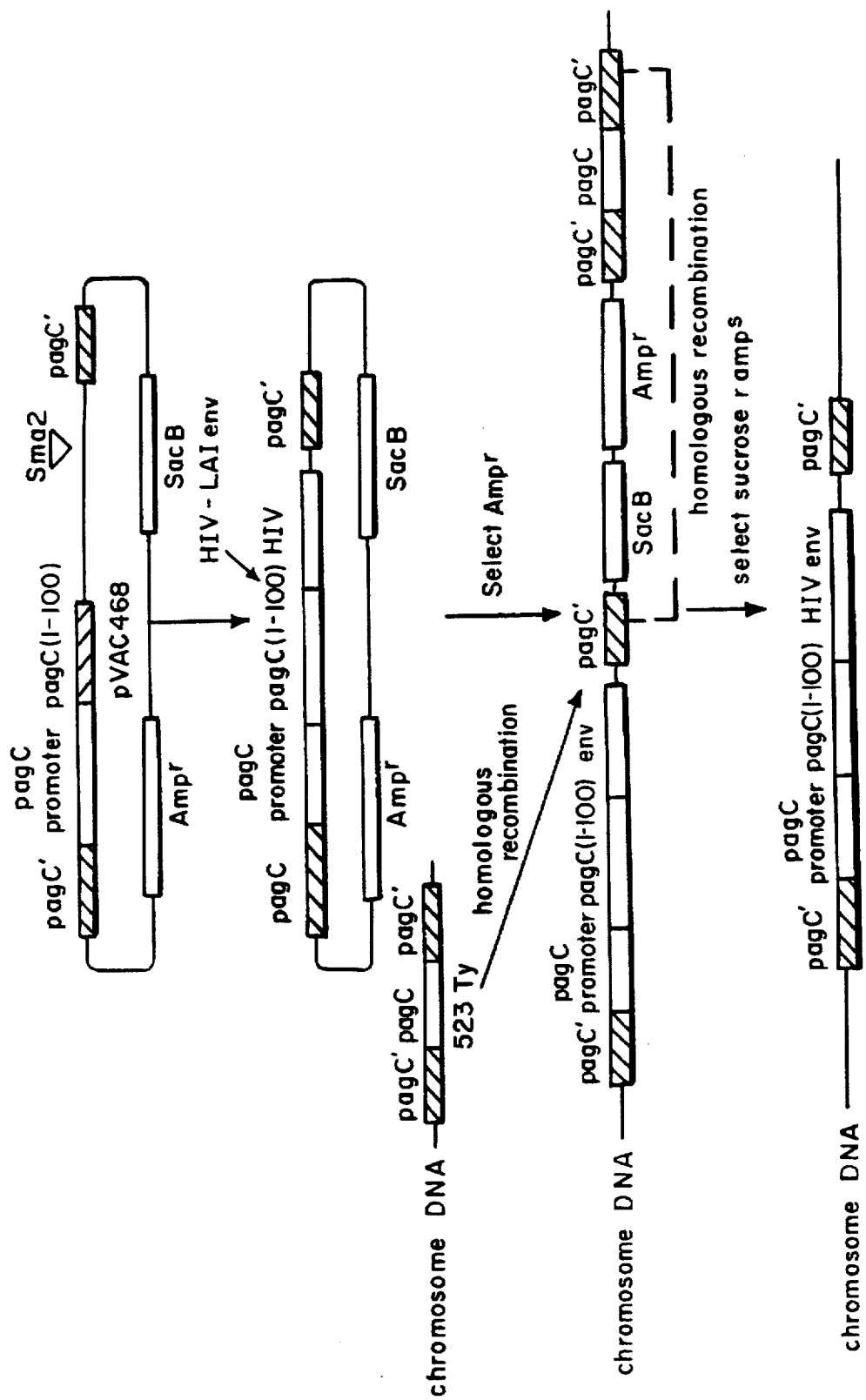
FIG. 3 is a schematic showing the use of pVAC468 to insert a gene encoding the HIV envelope protein in the manner described generally in FIG. 2.

The single recombination of pVAC468 into the Salmonella chromosome resulted in a duplication of pagC (FIGS. 2 and 3). A second homologous recombination event was required to remove the wild type copy of the pagC gene and the plasmid encoded ampicillin resistance gene from the chromosome. The *Bacillus subtilus* sacB gene encoding levansucrase was used to positively select for cells which had deleted the vector. The sacB gene has been demonstrated to be induced at 30° C. in the absence of NaCl [Blomfield, I. C., et al., *Mol. Microbiol.* 5:1447–1457 (1991)]. Under these conditions and in the presence of sucrose, the sacB gene product has been demonstrated to be lethal, and only cells which have deleted the gene should grow. Since it is possible to get spontaneous mutants which are able to grow in the presence of sucrose, sucrose resistant colonies were screened on ampicillin to determine which colonies no longer contained plasmid sequences.

Recombination events upstream and downstream of the wild type pagC are needed to replace it with the pagC104 allele (pagC104Δ). If both events occur on the same side of the gene, wild type pagC will be maintained. Therefore, the ampicillin sensitive colonies were screened on kanamycin to select for ones which had replaced TnphoA with pagC104Δ. 6 of the 25 ampicillin sensitive colonies were also kanamycin sensitive. The fact that a double recombination event had resulted in replacement of the pagC1::TnphoA allele with pagC104Δ was confirmed by Southern blot hybridization. Chromosomal DNAs were digested with the restriction endonuclease EcoRV, separated by agarose gel electrophoresis, blotted, and probed with a DNA fragment which contained pagC. If the wild type gene was present, a single 6.6 kilobase fragment would be observed. However, if the wild type gene had been replaced by pagC104Δ, digestion at the EcoRV restriction endonuclease site within the synthetic polylinker would generate two fragments of 2.2 and 3.9 kilobases (data not shown). One such strain was designated CS468 and was used for further virulence testing (see below).

Virulence Determination of Strain CS468.

Previous virulence data had shown that the pagC1::TnphoA mutation confers a virulence defect in BALB/c mice which can be complemented by the addition of a cosmid that carries the wild type pagC locus [Pulkkinen, W. S., et al., *J. Bacteriol.* 173:86–93 (1991)]. The TnphoA insertion within pagC appears to have no polar effect because the pagC transcript encodes a single envelope protein [Pulkkinen, J. Bacteriol. supra]. However, to formally prove the DNA encoding the pagC protein was essential to virulence, we tested strain CS468 for its effect on BALB/c mouse virulence. The pagC104Δmutation in CS468 was predicted to result in the synthesis of PagC deleted for its carboxy terminal 84 amino acids. The results of the mutation without expression of a fusion protein, the mutation and expression of a fusion protein are shown in in FIG. 7.

DNA fragment containing the HIV-HXB2 envelope gene, except for the first 220 amino acid was generated by PCR (HIV-HXB2 nucleotide sequence 6966 to 8795) and inserted into the SmaI site of the pVAC468 polylinker by the method described by the manufacturer to make an in frame fusion between the pagC gene and HIV-1 gene. The new salmonella shuttle plasmid, named pVACHIVE3, was confirmed by DNA sequencing. As a control to show that expression of HIV gene was directed by the pagC promoter, plasmid pVACHIVE3fs was constructed by the manner described above, having an additional base, G, added between the pagC and HIV genes so that HIV gene was frame shifted from the pagC gene.

pVACHIVE3 was introduced into a wild type *Salmonella typhimurium* strain, 10428, by conjugal transfer of the plasmid DNA from SM104Δpir as disclosed in [Simon, R., et al., *Bio/Tech* 1:784–791 (1983)]. As 10428 is ampicillin sensitive and the SM10Δpir can not grow efficiently on M9 medium which lacks leucine, threonine, and thiamine (M9LTT), the colonies that were able to grow on M9LTT plates with ampicillin were the 10428 hosts that acquired the shuttle plasmid. Because the plasmid is non-replicative in the salmonella strain, the bacteria must have acquired the plasmid DNA through a single homologous recombination between the pagC locus and the shuttle plasmid. In order to remove the wild type pagC gene and the antibiotics marker in the plasmid DNA, another homologous recombination was required. This was done by growing the bacteria in the presence of sucrose and in the absences of sodium chloride at 30° C. Under such conditions, the product of the sacB gene carried by the plasmid is toxic to the host. Therefore, the new derivatives from 10428 that were able to grow must be the bacteria that have removed the sacB gene and the wild type pagC gene through a single homologous recombination. The selection was confirmed by plating the bacteria on both the sucrose plate and the ampicillin plate. Those colonies that were sensitive to ampicillin but able to grow on sucrose plate were selected. Southern blot and Western blot analysis were performed to confirm the molecular construction of the new salmonella strain, named CSHIV101. By the same technique pVACHIVE3fs was introduced into strain 10428 to select CSHIVfs.

Figure 7:
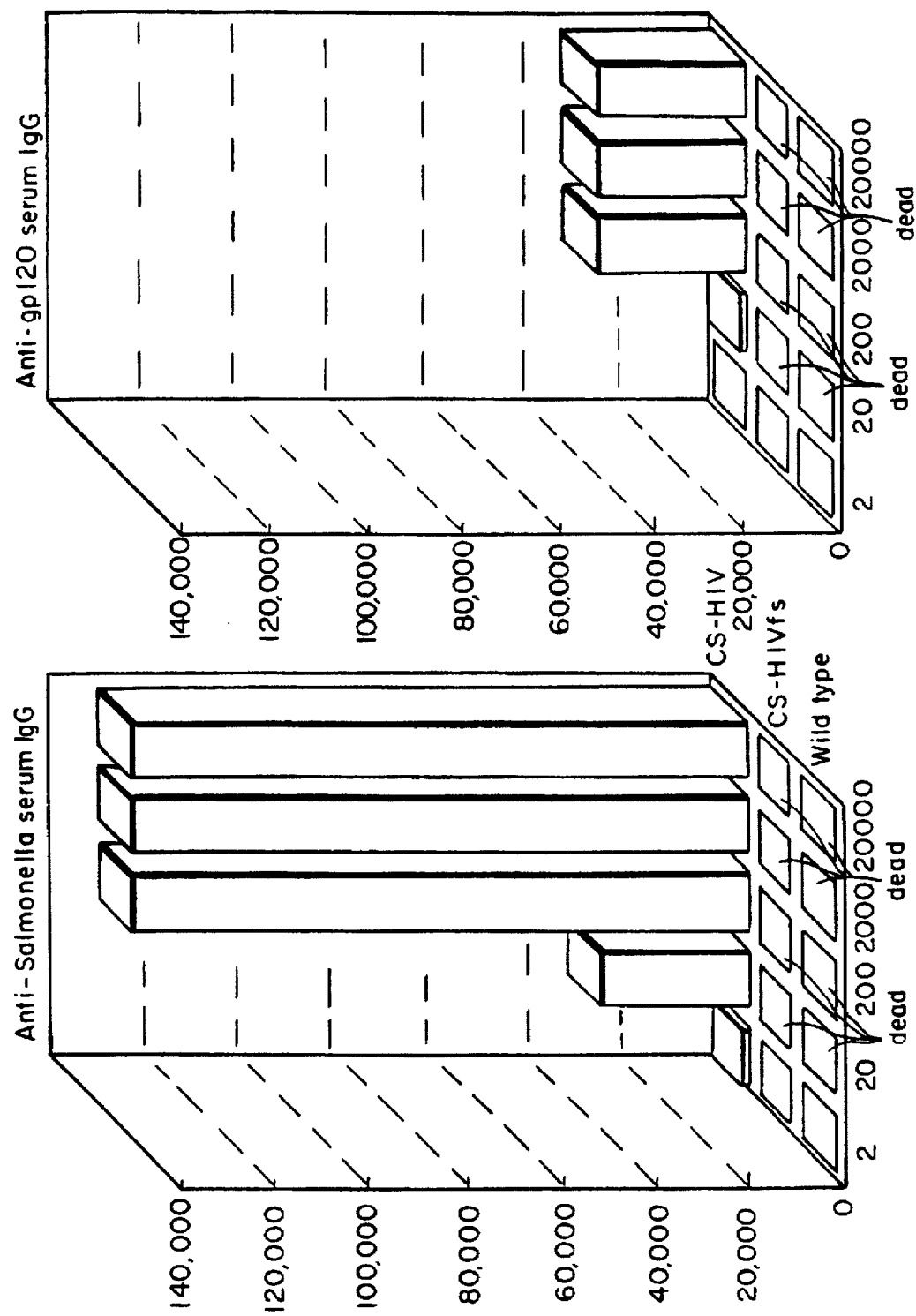
FIG. 7 shows the $LD_{50}$ of Salmonella CS119; CS-HIV-101; and the CS HIVfs in BALB/c-mice.
Figure 8:
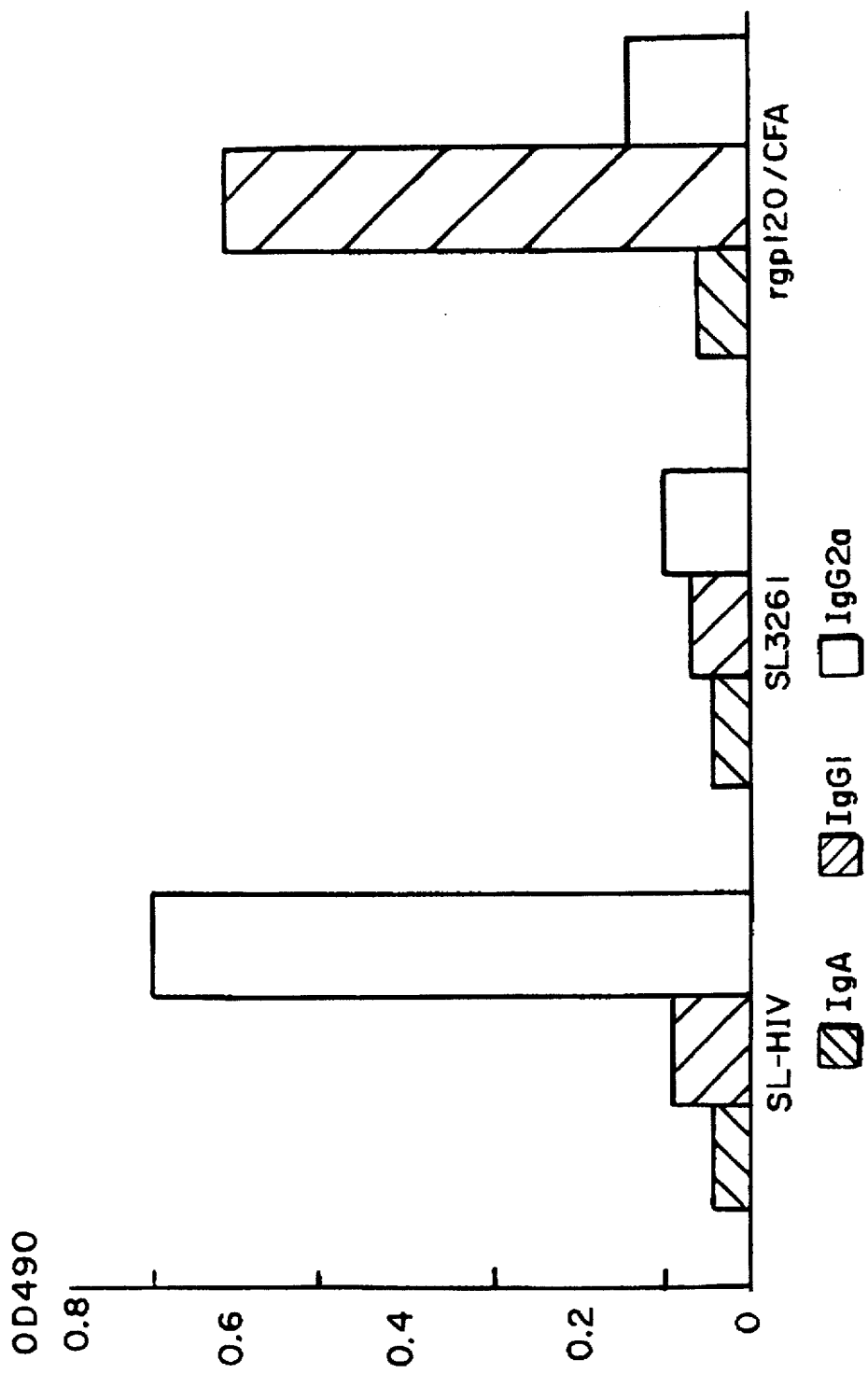
FIG. 8 shows the subtype of anti-HIV gp120 antibodies produced in BALB/c-mice immunized with Salmonella-HIV (SL-HIV), Salmonella (SL3261) and recombinant gp120 with complete Freund's Adjuvant (rgp 120/CFA).
Figure 9:
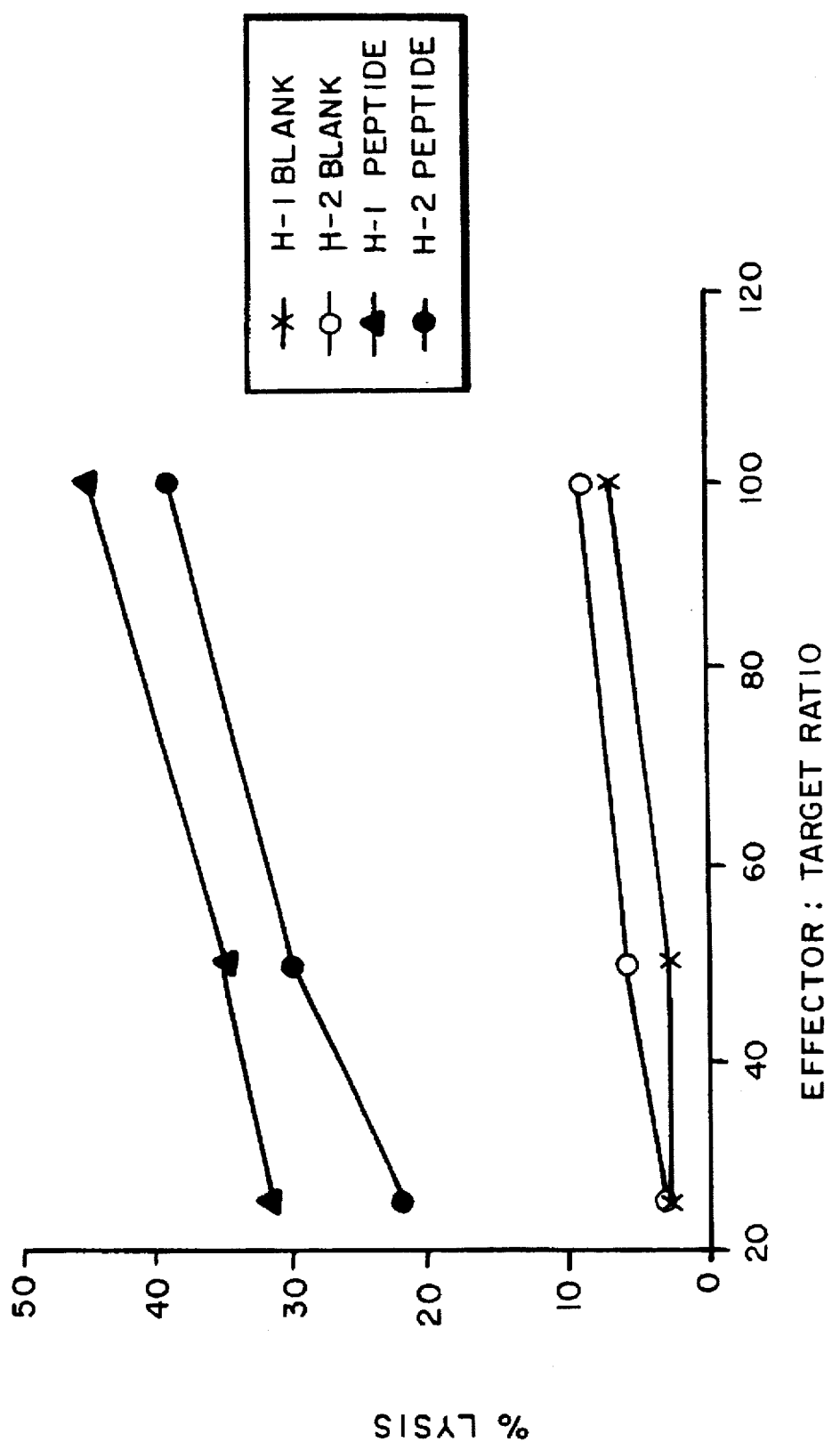
FIG. 9 shows the result of a Cytotoxic T Cell (CTL) assay with a Salmonella vector expressing the pagC fusion-gp120 protein.
Figure 10:
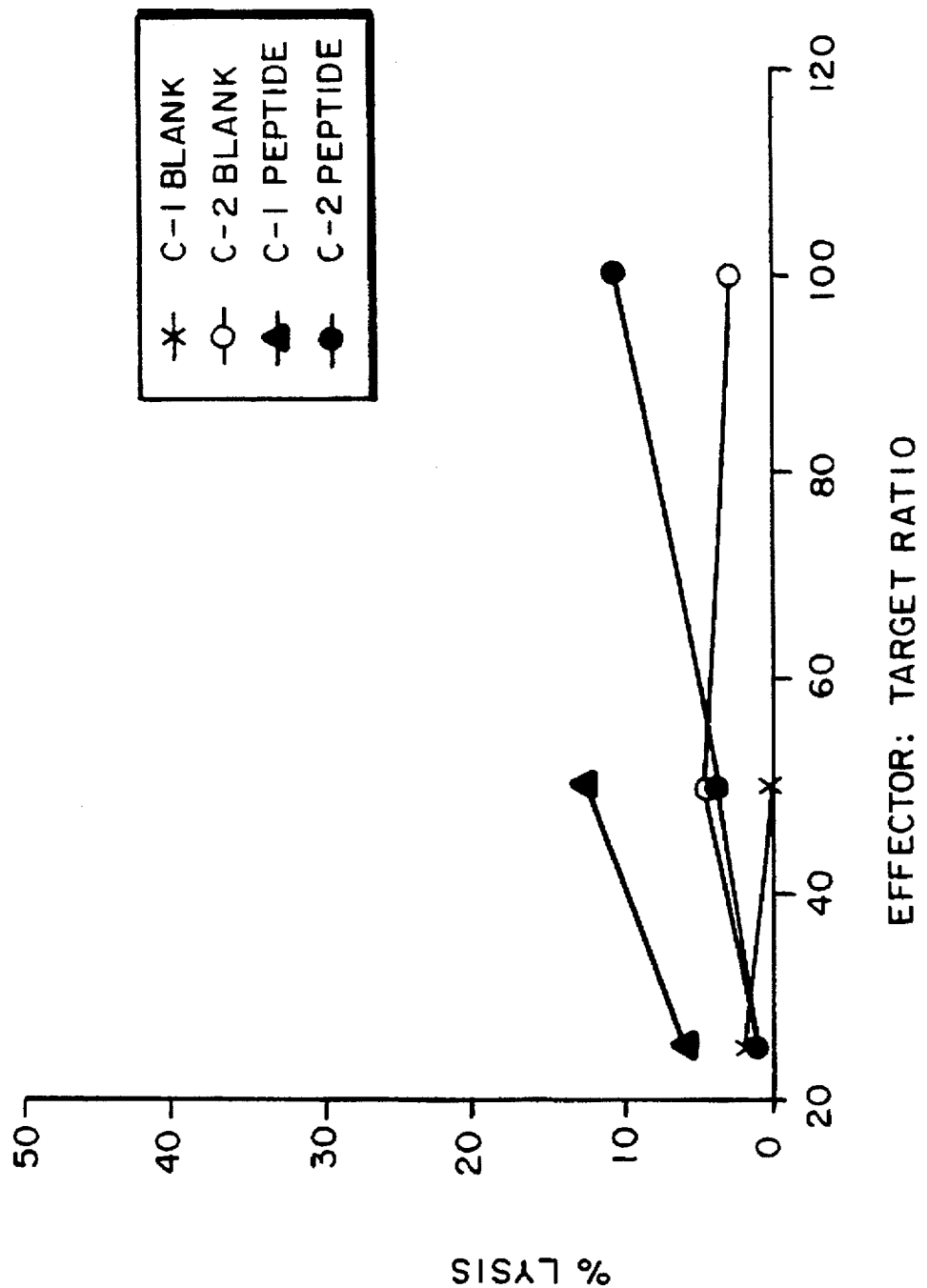
FIG. 10 shows a CTL assay using a similar vector to that described in FIG. 9 but expressing a fusion protein containing a different antigen, namely alkaline phosphatase (AP).

FIG. 7 shows the LD50 of CS468, CSHIV101, CSHIVfs in BALB/c mice administered by IP injection of different amounts of bacteria between 2 to 20,000 as indicated. It demonstrates that the genetic fusion of pagC gene and HIV envelope gene significantly attenuated the pathogenic effect of *Salmonella typhimurium* in mice ($LD_{50}$=20,000). However, it was only the fusion mutant (CSHIV101), not the deletion of pagC gene (CS468), that attenuated the bacteria. The conclusion is supported by the effect of mutant CSHIVfs, which is similar to that obtained with the CS468 vector ($LD_{50}$=2).

FIG. 6 shows expression of the HIV envelope protein expressed by a Salmonella vector after insertion of the gene encoding the HIV envelope using the pVAC468 vector. For the results depicted in this figure a human cell line derived from embryonic intestine, HI407(ATCC CCL6-HI407), was used to detect the expression of pagC-HIV fusion protein in Salmonella-HIV infected human macrophages. The experimental protocol was essentially the same as described by Mark Walker et al. [Infection and Immunity, vol. 60, page 4260 (1992)] with the following modification. The Salmonella-HIV infected HI407 cells were radiolabeled and the cell lysate was immunoprecipitated by monoclonal antibody against HIV gp120 (9284 DuPont/NEN). In FIG. 6, lane 1 is the HI407 cells infected with SL102 that contains the pagC-HIV fusion protein. Lane 2 is the HI407 cell without infection. Lane 3 is the cells infected with SL102 in which the pagC and HIV envelope genes are not fused. A detectable band in lane 1 represents the pagC-HIV fusion protein as detected by anti-gp120 antibody.

The serum from CSHIV101 immunized mice were examined by ELISA to detect antibodies against Salmonella antigens and HIV gp120 protein. As shown in FIG. 7, all the animals (three groups of four mice) that received more than 200 moi of CSHIV101 contain very high level of anti-salmonella serum IgG using ELISA plates coated with salmonella cell lysate. In these animals, significant level of anti-gp120 serum IgG was also detected.

The subtype of anti-gp120 antibodies in salmonella-HIV immunized mice was determined using different secondary antibodies purchased from Boehringer Mannheim. FIG. 8 shows the subtype of anti-HIV gp120 antibodies produced in BALB/c-mice immunized with Salmonella-HIV (SL-HIV), Salmonella (SL3261) and recombinant gp120 with complete Freund's Adjuvant (rgp 120/CFA). As shown in FIG. 8, the anti-gp120 antibodies appear to belong to the IgG2a subtype. When animals received recombinant HIV gp120 with complete Freund's adjuvant they developed mainly IgG1 antibodies. Therefore, it strongly suggests that salmonella-HIV is able to stimulate a Th1 mediated pathway towards cell mediated immune responses. These results also demonstrate that an immune response is obtained from the non-glycosylated envelope protein produced by bacteria, which is recognized by an HIV antibody.

The cytotoxic T-cell activity generated in response to the PagC-gp160 was further analyzed. Mice were immunized orally with $1\times10^8$ cfu of *S. typhimurium* CSO19 containing a single chromosomal copy of PagC-HIV gp160 (FIG. 9) or pagC-Alkaline phosphatase (PagC-AP) (control) (FIG. 10). Mice were sacrificed 5 weeks later and lymphocytes were harvested from spleens. Lymphocytes (effectors, E) were grown in vitro for 1 week in the presence of a 10 amino acid peptide (R10-1) from the V3 loop region of gp160 known to represent a ClassII-restricted HIV epitope for BABL/c mice. Target cells (T) were P815 cells (a mouse mastocytoma line) incubated for one hour with radiolabeled chromium, with (peptide) or without (blank) the same HIV V3 peptide. Effector cells and target cells were combined at various ratios at 37 C, and amount of large cell lysis was measured by scintillation counting of radiolabeled chromium released into the supernatant. Mice immunized with the strain carrying a PagC-HIV fusion protein developed T-cells able to lyse targets coated with peptide R10-I, while mice immunized with an irrelevant fusion (PagC-AP) were not able to produce significant lysis of the peptide coated targets. In the figures each set of experiments (i.e. with the gp160 fusions H- or with AP fusion, C-) was done with four mice, two with the R10-I peptide (filled in circle and triangle) (referred to as H/C-1 peptide and H/C-2 peptide) and two mice without peptide (X and O) (referred to as H/C-1 blank and H/C-2 blank).

Use of pVACHIVE3 to Replace pagC in S. typhi Strains.

The work described above used S. typhimurium strains which carry a pagC locus entirely homologous to the Salmonella DNA in pVAC468. We then attempted to use pVAC468 to make a deletion in the pagC locus of the S. typhi strain, CS125, which also carries the pagC1::TnphoA allele. Using the same techniques as described above, colonies in which pVAC468 had integrated into the pagC locus were obtained. After sucrose selection, 25 of the 32 sucrose resistant colonies tested had looped out the vector and replaced the pagC1::TnphoA allele with pagC104Δ. The presence of pagC104Δ and the absence of the wild type pagC gene was confirmed by Southern blot hybridization as described above (data not shown). One such S. typhi strain carrying pagC104Δ was designated Ty496. Therefore, we have demonstrated that pVAC468 can be used to delete pagC in Salmonella species other than S. typhimurium.

To test the ease of transferring pagC104Δ to candidate vaccine strains, the single recombinant strain Ty469/s was used as a donor of the pagC104 allele in a transductional cross with S. typhi strains 522Ty and 523Ty, candidate live vaccines containing aroA and hisG mutations [Edwards, M. F., et al., J. Bacteriol. 170:3991–3995 (1988)]. The crosses were done using P22HTint selection for ampicillin and kanamycin resistance. The sucrose selection described above was then performed to create the candidate vaccine strains, Ty476 and Ty475. Southern blot hybridization, as described above, was done to confirm the deletion of pagC. All of the ampicillin sensitive colonies screened by this method carried pagC104Δ (data not shown). Therefore, P22 transduction can be used to insert the integrated vector as well as the pagC1:TnphoA allele into any Salmonella vaccine candidate in order to facilitate the creation of pagC deletions.

Figure 4:
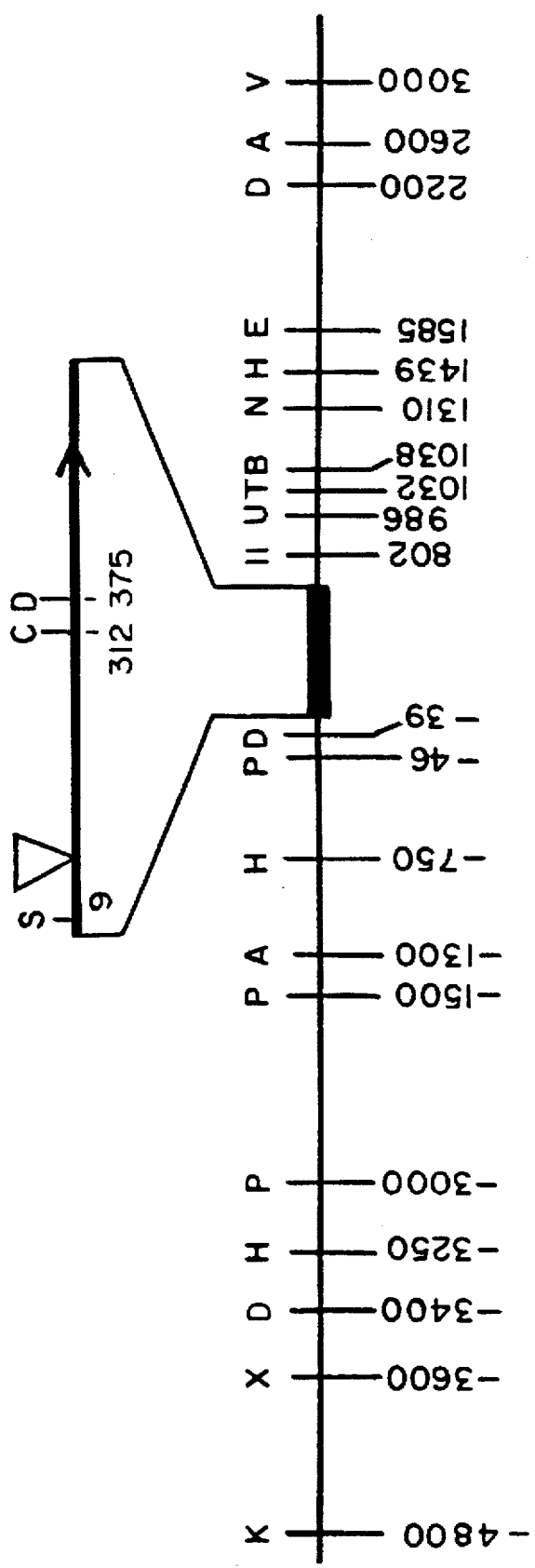
FIG. 4 is a map of the restriction endonuclease sites of the pagC locus.
Figure 6:
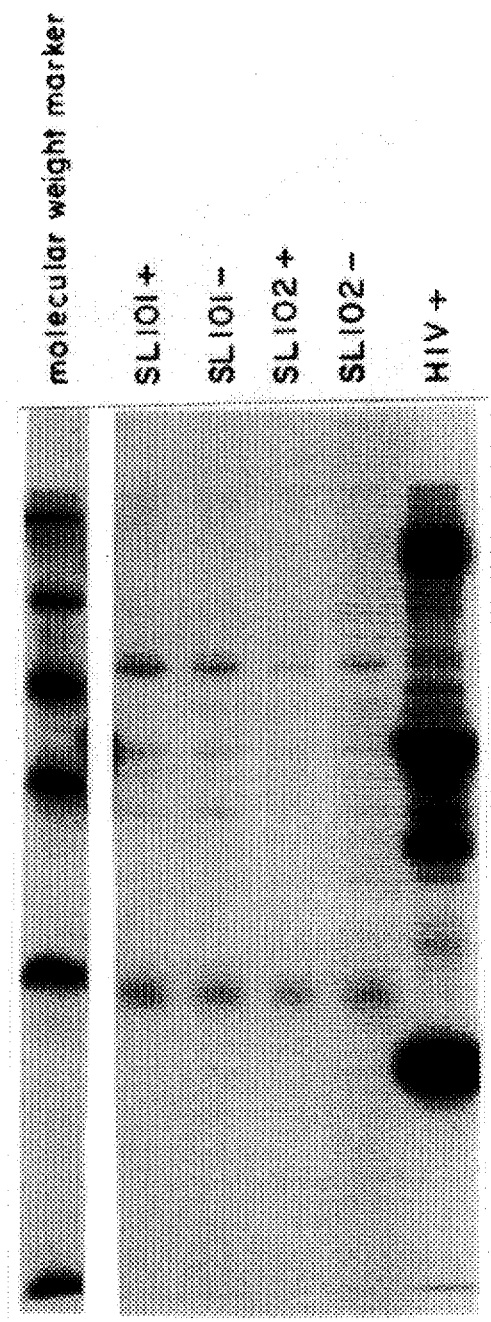
FIG. 6 shows expression of the HIV envelope protein expressed by a Salmonella vector after insertion of the gene encoding the HIV envelope using the pVAC468 vector. For the results depicted in this figure a human cell line derived from embryonic intestine, HI407 (ATCC CCL6-HI407), was used to detect the expression of pagC-HIV fusion protein in Salmonella-HIV infected human macrophages. The experimental protocol was essentially the same as described by Mark Walker et al. [Infection and Immunity, vol. 60, page 4260 (1992)] with the following modification. The salmonella-HIV infected HI407 cells were radio-active labeled and the cell lysate was immunoprecipitated by monoclonal antibody against HIV gp120 (9284 DuPont/NEN).

Physical mapping of restriction endonuclease sites, DNA sequencing, and determination of the pagC gene product. Restriction endonuclease analysis was performed to obtain a physical map of the pagC locus, and to determine the direction of transcription (FIG. 4). DNA subclones were generated and the TnphoA fusion junctions were sequenced, as well as the Salmonella DNA extending from the HpaI site, 828 nucleotide 5' to the phoA fusion junction, to the EcoRI site 1032 nucleotides 3' to the TnphoA insertion (FIGS. 4 and 5). The correct reading frame of the DNA sequence was deduced from that required to synthesize an active AP gene fusion. The deduced amino acid sequence of this open reading frame was predicted to encode a 188 amino acid protein with a predicted pI +8.2. This data were consistent with the 2-D polyacrylamide gel analysis of strain CS119 in which an 18 kDa protein of approximate pI +8.0 was absent. No other open reading frames, predicted to encode peptides larger than 30 amino acids, were found.

The deduced amino acid sequence of the 188 amino acid open reading frame contains a methionine start codon 33 amino acids from the fusion of pagC and AP (FIG. 5). This 33 amino acid pagC contribution to the fusion protein was consistent with the size observed in Western blot analysis and contains a hydrophobic N-terminal region, identified by the method of Kyle, et al., [J. Mol. Biol. 157:105–132 (1982), incorporated herein by reference], which is a typical bacterial signal sequence, [Von Heinje, J. Mol. Biol. 184:99–105 (1985) hereby incorporated by reference]. Specifically, amino acid 2 is a positively charge lysine, followed by a hydrophobic domain and amino acid 24 is a negatively charged aspartate residue. A consensus cleavage site for this leader peptide is predicted to be at an alanine residue at amino acid 23, [Von Heinje, J. Mol. Biol. 173:243–251 (1984), hereby incorporated by reference]. The DNA sequence also revealed a typical ribosome binding site, [Shine, et al., Proc. Natl. Acad. Sci. U.S.A., 71:1342–1346 (1974), hereby incorporated by reference] at 6-2 nucleotides 5' to the predicted start of translation (FIG. 5) (nucleotides 717–723). This suggested that the open reading frame was, in fact, translated and further supported the assumption that this was the deduced amino acid sequence of the pagC protein interrupted by the TnphoA insertion (FIG. 5).

Identification of the pagC Encoded RNA

An approximately 1100 nucleotide RNA is encoded by pagC. The pagC gene is highly expressed by cells with a phoP constitutive phenotype of pag activation, as compared to wild type and constitutive phenotype of pag activation, as compared to wild type and phoP bacteria. In these blot hybridization experiments pagC is only detected in wild type cells grown in rich media during stationary growth. This result, coupled with previous work, Miller, et al., 1989, supra, Miller et al., 1990, supra, demonstrates that pagC is transcriptionally regulated by the phoP gene products and is only expressed during early logarithmic phase growth in rich media by cells with a phoP constitutive phenotype.

The size of the pagC transcript is approximately 500 nucleotides greater than that necessary to encode the 188 amino acid protein. Primer extension analysis of Salmonella RNA using oligonucleotide primers specific for pagC sequence was performed to determine the approximate start site of transcription and to determine whether these nucleotides might be transcribed 5' or 3' to the 188 amino acid pagC gene product. Primer extension analysis with an oligonucleotide predicted to be complementary to nucleotides 550–365 of pagC, 150 nucleotides 5' to the predicted start codon, resulted in an approximately 300 nucleotide primer extension product. Therefore, a primer further upstream was constructed complementary to nucleotides 335–350 of pagC and used in a similar analysis. A primer extension product of 180 nucleotides was observed to be primer specific. This is consistent with transcription starting at nucleotide 170 (FIG. 5). Upstream of the predicted transcriptional start, at nucleotides 153–160, a classic RNA polymerase binding site was observed with the sequence TATAAT at -12 nucleotides as well as the sequence TAATAT at -10 nucleotides. No complete matches were observed for the consensus RNA polymerase recognition site (TTGACA) 15–21 nucleotides upstream from the -10 region. AT -39 (126–131) nucleotides (TTGGAA), -38 (127–132) nucleotides (TTGTGG), and -25 (135–140) nucleotides (TTGATT) are sequences that have matches with the most frequently conserved nucleotides of this sequence.

23

Based on the above results, transcription was predicted to terminate near the translational stop codon of the 188 amino acid protein (nucleotide 1295, FIG. 5). Indeed, a stem loop configuration was found at nucleotides 1309–1330 that may function as a transcription terminator. This was consistent with the lack of evidence of open reading frames downstream of the 188 amino acid protein and the lack of synthesis of other transcription/translation using the cloned pagC DNA.

24

It is evident that those skilled in the art, given the benefit of the foregoing disclosure, may make numerous modifications thereof and departures from the specific embodiments described without departing from the inventive concepts and the present invention is to be limited solely by the scope and spirit of the appended claims.

We claim:

1. A Salmonella bacteria vector containing a sufficient portion of a Salmonella genome for replication and infection, wherein a native wild type pagC gene in the Salmonella genome has been modified to contain a partial deletion in the pagC gene by the insertion of a DNA fragment encoding a truncated pagC protein that has a deletion of the eighty-four amino acids from the carboxy terminus, said deletion attenuating the virulence of said Salmonella bacteria vector, and wherein said pagC DNA fragment is linked in frame to a heterologous DNA segment to create a pag-fusion protein gene which encodes a pag-fusion protein which is operably linked to an in vivo inducible promoter.

2. The vector of claim 1 wherein said DNA fragment encodes the pagC leader sequence.

3. The vector of claim 1 wherein said heterologous DNA segment encodes an immunogenic epitope.

4. The vector of claim 3 wherein said heterologous DNA segment encodes an antigen of a bacteria, a virus, or a parasite.

5. The vector of claim 4, wherein said antigen is a viral antigen selected from the group consisting of antigens of lentiviruses and persistent infectious viruses.

6. The vector of claim 4 wherein said viral antigen is a viral antigen of an HIV virus or a hepatitis virus.

7. The vector of claim 6 wherein said viral antigen is selected from the group consisting of an HIV envelope antigen, an HIV gag antigen, an HIV nef antigen, a hepatitis B surface antigen and a hepatitis C surface antigen.

8. The vector of claim 1 wherein said heterologous DNA segment encodes a portion of the HIV envelope glycoprotein containing the principle neutralizing domain.

9. The vector of claim 1 wherein said Salmonella genome is selected from the group consisting of S. typhi, S. enteriditis, S. typhimurium, S. choleraesuis, S. typhimurium, S. paratyphi A, S paratyphi B, S. paratyphi C, S. pylorum, S. dublin, S. heidelberg, S. newport, S. minnesota, S. infantis, S. virchow, and S. panama.

10. The vector of claim 1 wherein said in vivo inducible promoter is a macrophage inducible promoter.

11. The vector of claim 10 wherein said macrophage inducible promoter is a promoter for a pag gene.

12. The vector of claim 11 wherein said promoter is a pagC promoter.

13. A method of producing an attenuated Salmonella bacteria vector in accordance with claim 1, which comprises modifying a Salmonella genome by replacing a pagC gene with a truncated pagC gene that has a deletion of the eighty-four amino acids from the carboxy terminus, said truncated pagC gene linked in frame to a heterologous DNA segment to encode a truncated pag-fusion protein.

* * * * *

UNITED STATES PATENT AND TRADEMARK OFFICE
CERTIFICATE OF CORRECTION

PATENT NO. : 5,733,760
DATED : March 31, 1998
INVENTOR(S) : Y. Lu, et al

It is certified that error appears in the above-identified patent and that said Letters Patent is hereby corrected as shown below:

Col. 1, line 44, replace "then" with --than--;

Col. 6, lines 5-7, delete ", another proposed vaccine suffers from being invasive and having some incidence of systemic spread";

Col. 7, line 47, replace "p/r" with --pir--;

Col. 7, line 48, replace "salmonella" with --Salmonella--;

Col. 7, line 52, delete "]";

Col. 7, line 54, replace "salmonella" with --Salmonella--;

Col. 7, line 58, replace "resistant" with --resistance--;

Col. 7, line 61, replace "sties" with --sites--;

UNITED STATES PATENT AND TRADEMARK OFFICE
CERTIFICATE OF CORRECTION

PATENT NO. : 5,733,760
DATED : March 31, 1998
INVENTOR(S) : Y. Lu, et al

It is certified that error appears in the above-identified patent and that said Letters Patent is hereby corrected as shown below:

Col. 8, line 19, replace "peptide" with --peptides--;

Col. 8, line 39, replace "acid" with --acids--;

Col. 8, line 41, replace "the SmaI site to make a" with --SmaI to make an--;

Col. 9, line 30, replace "conserved," with --conserved.--;

Col. 12, line 7, replace "salmonella" with --Salmonella--;

Col. 12, line 45, add --antibodies-- after "anti-gp120";

Col. 12, line 50, delete "viral";

Col 15, Table 1, replace "Kileen" with --Killeen--;

Col. 15, Table 1, footnote b, replace "Bacterioil" with --Bacteriol--;

Col. 17, line 20, replace "*Typhimurium*" with --*typhimurium*--;

Col. 18, line 28, replace "CSO14" (with a zero) with --CSO14--;

UNITED STATES PATENT AND TRADEMARK OFFICE
CERTIFICATE OF CORRECTION

PATENT NO. : 5,733,760                        Page 3 of 4
DATED : March 31, 1998
INVENTOR(S) : Y. Lu, et al It is certified that error appears in the above-identified patent and that said Letters Patent is hereby corrected as shown below:

Col. 18, line 31, replace "TrphoA" with --TnphoA--;

Col. 19, line 36, replace "salmonella" with --Salmonella--;

Col. 19, line 39, add --the-- before "HIV";

Col. 20, line 3, replace "salmonella" with --Salmonella--;

Col. 20, line 41, replace "salmonella" with --Salmonella--;

Col. 20, line 42, replace "salmonella" with --Salmonella--;

Col. 20, line 44, replace "salmonella" with --Salmonella--;

Col. 20, line 54, replace "salmonella" with --Salmonella--;

Col. 20, line 61, replace "PagC-gp160" with --pagC-gp160--;

Col. 20, line 64, replace "pagC-Alkaline" with --pagC-alkaline--;

UNITED STATES PATENT AND TRADEMARK OFFICE
CERTIFICATE OF CORRECTION

PATENT NO. : 5,733,760
DATED : March 31, 1998
INVENTOR(S) : Y. Lu, et al

It is certified that error appears in the above-identified patent and that said Letters Patent is hereby corrected as shown below:

Col. 21, line 4, replace "37 C" with --37° C--;

Col. 21, line 10, replace "PagC-HIV" with --pagC-HIV--.

Signed and Sealed this

Eighth Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 2319 base pairs
( B ) TYPE: nucleic acid
( C ) STRANDEDNESS: unknown
( D ) TOPOLOGY: unknown ( i x ) FEATURE:
( A ) NAME/KEY: CDS
( B ) LOCATION: 729..1292

( x i ) SEQUENCE DESCRIPTION: SEQ ID NO:1:

```
GTTAACCACT  CTTAATAATA  ATGGGTTTTA  TAGCGAAATA  GACTTTTTA  TCGCGTGTTC     60

AATATTTGCG  TTAGTTATTA  TTTTTTTGGA  ATGTAAATTC  TCTCTAAACA  CAGGTGATAT    120

TTATGTTGGA  ATTGTGGTGT  TGATTCTATT  CTTATAATAT  AACAAGAAAT  GTTGTAACTG    180

ATAGATATAT  TAAAAGATTA  AATCGGAGCG  GGAATAAAGC  GTGCTAAGCA  TCATCGTGAA    240

TATGATTACA  GCGCCTGCGA  TGGCATATAA  CCGTATTGCG  GATGGAGCGT  CACGTGAGGA    300

CTGTGAAGCA  CAATGCGATA  TGTTCTGATT  ATATGGCGAG  TTTGCTTAAT  GACATGTTTT    360

TAGCCGAACG  GTGTCAAGTT  TCTTAATGTG  GTTGTGAGAT  TTTCTCTTTA  AATATCAAAA    420

TGTTGCATGG  GTGATTTGTT  GTTCTATAGT  GGCTAAACAC  TTTATGGTTT  CTGTTAAATA    480

TATATGCGTG  AGAAAAATTA  GCATTCAAAT  CTATAAAAGT  TAGATGACAT  TGTAGAACCG    540

GTTACCTAAA  TGAGCGATAG  AGTGCTTCGG  TAGTAAAAAT  ATCTTTCAGG  AAGTAAACAC    600

ATCAGGAGCG  ATAGCGGTGA  ATTATTCGTG  GTTTTGTCGA  TTCGGCATAG  TGGCGATAAC    660

TGAATGCCGG  ATCGGTACTG  CAGGTGTTTA  AACACACCGT  AAATAATAAG  TAGTATTAAG    720

GAGTTGTT ATG AAA AAT ATT ATT TTA TCC ACT TTA GTT ATT ACT ACA AGC         770
         Met Lys Asn Ile Ile Leu Ser Thr Leu Val Ile Thr Thr Ser
         1               5                   10

GTT TTG GTT GTA AAT GTT GCA CAG GCC GAT ACT AAC GCC TTT TCC GTG         818
Val Leu Val Val Asn Val Ala Gln Ala Asp Thr Asn Ala Phe Ser Val
15                  20                  25                  30

GGG TAT GCA CGG TAT GCA CAA AGT AAA GTT CAG GAT TTC AAA AAT ATC         866
Gly Tyr Ala Arg Tyr Ala Gln Ser Lys Val Gln Asp Phe Lys Asn Ile
                35                  40                  45

CGA GGG GTA AAT GTG AAA TAC CGT TAT GAG GAT GAC TCT CCG GTA AGT         914
Arg Gly Val Asn Val Lys Tyr Arg Tyr Glu Asp Asp Ser Pro Val Ser
            50                  55                  60

TTT ATT TCC TCG CTA AGT TAC TTA TAT GGA GAC AGA CAG GCT TCC GGG         962
Phe Ile Ser Ser Leu Ser Tyr Leu Tyr Gly Asp Arg Gln Ala Ser Gly
        65                  70                  75

TCT GTT GAG CCT GAA GGT ATT CAT TAC CAT GAC AAG TTT GAG GTG AAG        1010
Ser Val Glu Pro Glu Gly Ile His Tyr His Asp Lys Phe Glu Val Lys
```

|  |  |  |  |  | 80 |  |  |  |  | 85 |  |  |  |  | 90 |  |  |  |  |
|---|---|---|---|---|---|---|---|---|---|---|---|---|---|---|---|---|---|---|---|---|
| TAC | GGT | TCT | TTA | ATG | GTT | GGG | CCA | GCC | TAT | CGA | TTG | TCT | GAC | AAT | TTT | | | | | 1058 |
| Tyr | Gly | Ser | Leu | Met | Val | Gly | Pro | Ala | Tyr | Arg | Leu | Ser | Asp | Asn | Phe | | | | | |
| 95 | | | | | 100 | | | | | 105 | | | | | 110 | | | | | |
| TCG | TTA | TAC | GCG | CTG | GCG | GGT | GTC | GGC | ACG | GTA | AAG | GCG | ACA | TTT | AAA | | | | | 1106 |
| Ser | Leu | Tyr | Ala | Leu | Ala | Gly | Val | Gly | Thr | Val | Lys | Ala | Thr | Phe | Lys | | | | | |
| | | | | 115 | | | | | 120 | | | | | 125 | | | | | | |
| GAA | CAT | TCC | ACT | CAG | GAT | GGC | GAT | TCT | TTT | TCT | AAC | AAA | ATT | TCC | TCA | | | | | 1154 |
| Glu | His | Ser | Thr | Gln | Asp | Gly | Asp | Ser | Phe | Ser | Asn | Lys | Ile | Ser | Ser | | | | | |
| | | | 130 | | | | | 135 | | | | | 140 | | | | | | | |
| AGG | AAA | ACG | GGA | TTT | GCC | TGG | GGC | GCG | GGT | GTA | CAG | ATG | AAT | CCG | CTG | | | | | 1202 |
| Arg | Lys | Thr | Gly | Phe | Ala | Trp | Gly | Ala | Gly | Val | Gln | Met | Asn | Pro | Leu | | | | | |
| | | 145 | | | | | 150 | | | | | 155 | | | | | | | | |
| GAG | AAT | ATC | GTC | GTC | GAT | GTT | GGG | TAT | GAA | GGA | AGC | AAC | ATC | TCC | TCT | | | | | 1250 |
| Glu | Asn | Ile | Val | Val | Asp | Val | Gly | Tyr | Glu | Gly | Ser | Asn | Ile | Ser | Ser | | | | | |
| | | 160 | | | | | 165 | | | | | 170 | | | | | | | | |
| ACA | AAA | ATA | AAC | GGC | TTC | AAC | GTC | GGG | GTT | GGA | TAC | CGT | TTC | | | | | | | 1292 |
| Thr | Lys | Ile | Asn | Gly | Phe | Asn | Val | Gly | Val | Gly | Tyr | Arg | Phe | | | | | | | |
| 175 | | | | | 180 | | | | | 185 | | | | | | | | | | |

| | | | | | |
|---|---|---|---|---|---|
| TGAAAAGCAT | AAGCTATGCG | GAAGGTTCGC | CTTCCGCACC | GCCAGTCAAT | AAAACAGGGC | 1352 |
| TTCTTTACCA | GTGACACGTA | CCTGCCTGTC | TTTTCTCTCT | TCGTCATACT | CTCTTCGTCA | 1412 |
| TAGTGACGCT | GTACATAACA | TCTCACTAGC | ATAAGCACAG | ATAAGGATT | GTGGTAAGCA | 1472 |
| ATCAAGGTTG | CTCAGGTAGG | TGATAAGCAG | GAAGGAAAAT | CTGGTGTAAA | TAACGCCAGA | 1532 |
| TCTCACAAGA | TTCACTCTGA | AAAATTTTCC | TGGAATTAAT | CACAATGTCA | TCAAGATTTT | 1592 |
| GTGACCGCCT | TCGCATATTG | TACCTGCCGC | TGAACGACTA | CTGAAAAGTA | GCAAGGTATG | 1652 |
| TATTTTATCC | AGGAGAGCAC | CTTTTTTGCG | CCTGGCAGAA | GTCCCCAGCC | GCCACTAGCT | 1712 |
| CAGCTGGATA | GAGCATCAAC | CTCCTAAGTT | GATGGTGCGA | GGTTCGAGGC | CTCGGTGGCG | 1772 |
| GTCCAATGTG | GTTATCGTAT | AATGTTATTA | CCTCAGTGTC | AGGCTGATGA | TGTGGGTTCG | 1832 |
| ACTCCCACTG | ACCACTTCAG | TTTTGAATAA | GTATTGTCTC | GCAACCCTGT | TACAGAATAA | 1892 |
| TTTCATTTAT | TACGTGACAA | GATAGTCATT | TATAAAAAAT | GCACAAAAAT | GTTATTGTCT | 1952 |
| TTTATTACTT | GTGAGTTGTA | GATTTTCTT | ATGCGGTGAA | TCCCCCTTTG | CGGCGGGGCG | 2012 |
| TCCAGTCAAA | TAGTTAATGT | TCCTCGCGAA | CCATATTGAC | TGTGGTATGG | TTCACCGGGA | 2072 |
| GGCACCCGGC | ACCGCAATTT | TTTATAAAAT | GAAATTCACA | CCCTATGGTT | CAGAGCGGTG | 2132 |
| TCTTTTTACA | TCAGGTGGGC | AAGCATAATG | CAGGTTAACT | TGAAAGATAC | GATCAATAGC | 2192 |
| AGAAACCAGT | GATTTCGTTT | ATGGCCTGGG | GATTTAACCG | CGCCAGAGCG | TATGCAAGAC | 2252 |
| CCTGGCGCGG | TTGGCCGGTG | ATCGTTCAAT | AGTGCGAATA | TGAATGGTTA | CCAGCCGCTG | 2312 |
| CGAATTC | | | | | | 2319 |

( 2 ) INFORMATION FOR SEQ ID NO:2:

( i ) SEQUENCE CHARACTERISTICS:
        ( A ) LENGTH: 53 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

CATTTCTCAT TGATAATGAG AATCATTATT GACATAATTG TTATTATTTT ACG      53

( 2 ) INFORMATION FOR SEQ ID NO:3:

( i ) SEQUENCE CHARACTERISTICS:
        ( A ) LENGTH: 188 amino acids (B) TYPE: amino acid
(D) TOPOLOGY: linear (ii) MOLECULE TYPE: protein (xi) SEQUENCE DESCRIPTION: SEQ ID NO:3:

```
Met Lys Asn Ile Ile Leu Ser Thr Leu Val Ile Thr Thr Ser Val Leu
 1               5                  10                  15
Val Val Asn Val Ala Gln Ala Asp Thr Asn Ala Phe Ser Val Gly Tyr
             20                  25                  30
Ala Arg Tyr Ala Gln Ser Lys Val Gln Asp Phe Lys Asn Ile Arg Gly
         35                  40                  45
Val Asn Val Lys Tyr Arg Tyr Glu Asp Asp Ser Pro Val Ser Phe Ile
     50                  55                  60
Ser Ser Leu Ser Tyr Leu Tyr Gly Asp Arg Gln Ala Ser Gly Ser Val
 65                  70                  75                  80
Glu Pro Glu Gly Ile His Tyr His Asp Lys Phe Glu Val Lys Tyr Gly
                 85                  90                  95
Ser Leu Met Val Gly Pro Ala Tyr Arg Leu Ser Asp Asn Phe Ser Leu
            100                 105                 110
Tyr Ala Leu Ala Gly Val Gly Thr Val Lys Ala Thr Phe Lys Glu His
        115                 120                 125
Ser Thr Gln Asp Gly Asp Ser Phe Ser Asn Lys Ile Ser Ser Arg Lys
    130                 135                 140
Thr Gly Phe Ala Trp Gly Ala Gly Val Gln Met Asn Pro Leu Glu Asn
145                 150                 155                 160
Ile Val Val Asp Val Gly Tyr Glu Gly Ser Asn Ile Ser Ser Thr Lys
                165                 170                 175
Ile Asn Gly Phe Asn Val Gly Val Gly Tyr Arg Phe
                180                 185
```

(2) INFORMATION FOR SEQ ID NO:4:

(i) SEQUENCE CHARACTERISTICS:
(A) LENGTH: 32 base pairs
(B) TYPE: nucleic acid
(C) STRANDEDNESS: unknown
(D) TOPOLOGY: unknown (xi) SEQUENCE DESCRIPTION: SEQ ID NO:4:

CGATATCTCG AGCTCGTCGA CCCGGGTCTA GA    32

(2) INFORMATION FOR SEQ ID NO:5:

(i) SEQUENCE CHARACTERISTICS:
(A) LENGTH: 34 base pairs
(B) TYPE: nucleic acid
(C) STRANDEDNESS: unknown
(D) TOPOLOGY: unknown (xi) SEQUENCE DESCRIPTION: SEQ ID NO:5:

GATCTCTAGA CCCGGGTCGA CGAGCTCGAG ATCT    34